US008885918B2

(12) United States Patent
Amanullah et al.

(10) Patent No.: US 8,885,918 B2
(45) Date of Patent: Nov. 11, 2014

(54) SYSTEM AND METHOD FOR INSPECTING A WAFER

(75) Inventors: Ajharali Amanullah, Singapore (SG); Albert Archwamety, Singapore (SG); Hongtu Guo, Singapore (SG)

(73) Assignee: Semiconductor Technologies & Instruments Pte Ltd (SG)

( * ) Notice: Subject to any disclaimer, the term of this patent is extended or adjusted under 35 U.S.C. 154(b) by 818 days.

(21) Appl. No.: 12/657,076

(22) Filed: Jan. 13, 2010

(65) Prior Publication Data

US 2010/0189339 A1 Jul. 29, 2010

(30) Foreign Application Priority Data

Jan. 13, 2009 (SG) .................................. 200900229
Feb. 16, 2009 (SG) .................................. 200901110

(51) Int. Cl.
*G06K 9/00* (2006.01)

(52) U.S. Cl.
USPC .......................................... 382/145; 382/141

(58) Field of Classification Search
CPC .................. G01N 2021/8825; G01N 21/8806; G01N 21/9501; G06T 2207/10152; G06T 2207/20212; G06T 2207/30148; G06T 7/001; G06T 7/401; H01L 22/12
USPC ......... 382/144–152, 154, 256, 266–269, 212, 382/213, 214, 284–286; 356/237.1–237.6; 250/306, 216, 200, 559.01, 559.4, 250/559.41–559.46; 226/20; 101/484
See application file for complete search history.

(56) References Cited

U.S. PATENT DOCUMENTS

| 7,729,528 B2 * | 6/2010 | O'Dell et al. ................. 382/149 |
| 2005/0110987 A1 * | 5/2005 | Furman et al. ............ 356/237.4 |

FOREIGN PATENT DOCUMENTS

| JP | 2005-077109 | 3/2005 |
| JP | 2007156262 A * | 6/2007 | .................... 382/149 |

* cited by examiner

*Primary Examiner* — Tri T Ton
(74) *Attorney, Agent, or Firm* — Axis Intellectual Capital Pte Ltd

(57) ABSTRACT

A method for inspecting a wafer. The method comprises a training process for creating reference images. The training process comprises capturing a number of images of a first wafer of unknown quality, each of the number of images of the first wafer being captured at a predetermined contrast illumination and each of the number of images of the first wafer comprising a plurality of pixels. The training process also comprises determining a plurality of reference intensities for each of the plurality of pixels of each of the number of images of the first wafer, calculating a plurality of statistical parameters for the plurality of reference intensities of each of the plurality of pixels of each of the number of images of the first wafer, and selecting a plurality of reference images from the plurality of images of the first wafer based on the calculated plurality of statistical parameters. The method for inspecting the wafer further comprises capturing an image of a second wafer, the second wafer being of an unknown quality, selecting a first reference image from the plurality of reference images, and comparing the captured image of the second wafer with the first reference image to thereby determine at least one of presence and type of defect on the second wafer.

22 Claims, 26 Drawing Sheets

Table of Illumination Configurations Selectable by Illumination Configurator

| Configuration | First Illumination Supplied | Second Illumination Supplied |
|---|---|---|
| 1 | Brightfield | High Angle Darkfield |
| 2 | Brightfield | Low Angle Darkfield |
| 3 | Brightfield + High Angle Darkfield | High Angle Darkfield |
| 4 | Brightfield + High Angle Darkfield | Low Angle Darkfield |
| 5 | Brightfield | High Angle Darkfield + Low Angle Darkfield |
| 6 (with same illumination but varying intensity level) | Brightfield with intensity level (e.g. 50%) | Brightfield with intensity level (e.g. 25%) |
| 7 | High Angle Darkfield | Brightfield |
| 8 | Brightfield + High Angle Darkfield | Brightfield + Low Angle Darkfield |
| 9 | High Angle Darkfield with intensity level (e.g. 60%) | High Angle Darkfield with intensity level (e.g. 50%) |

FIG. 20

Timing chart of 2D image acquisition from first and second image capture devices FIG. 22a First Image 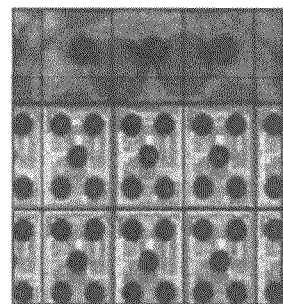   FIG. 22b Second Image 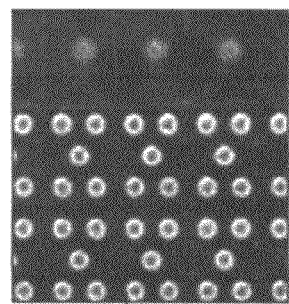
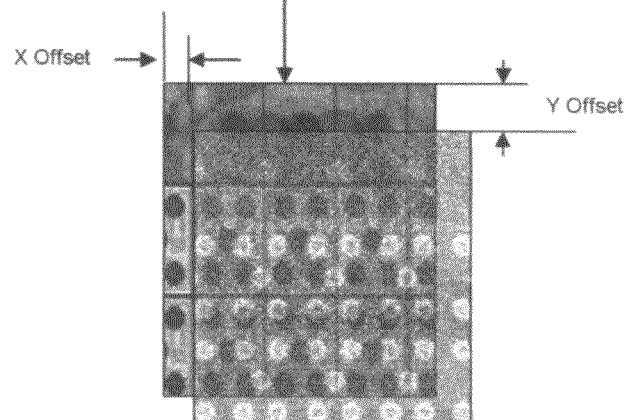
FIG. 22c Combined first Image and second image demonstrating image offset due to image capture while wafer is moving

SYSTEM AND METHOD FOR INSPECTING A WAFER

FIELD OF INVENTION

The present invention relates generally to a wafer inspection process. More specifically, the present invention relates to an automated system and method for inspecting semiconductor components.

BACKGROUND

The ability to ensure a consistently high quality of manufactured semiconductor components, for example semiconductor wafers and dies, is increasingly crucial in the semiconductor industry. Semiconductor wafer fabrication techniques have been consistently improved to incorporate an increasing number of features into a smaller surface area of the semiconductor wafer. Accordingly, the photolithographic processes used for semiconductor wafer fabrication has become more sophisticated to allow the incorporation of increasing features to the smaller surface area of the semiconductor wafer (i.e. higher performance of the semiconductor wafer). Consequently, sizes of potential defects on semiconductor wafers are typically in the micron to submicron range.

It is evident that manufacturers of semiconductor wafers have an increasingly pressing need to improve semiconductor wafer quality control and inspection procedures to ensure a consistently high quality of manufactured semiconductor wafers. Semiconductor wafers are typically inspected for detecting defects thereon, such as presence of surface particulates, imperfections, undulations and other irregularities. Such defects could affect eventual performance of the semiconductor wafers. Therefore, it is critical to eliminate or extract defective semiconductor wafers during the manufacture thereof.

There have been advances in semiconductor inspection systems and processes. For example, higher resolution imaging systems, faster computers, and enhanced precision mechanical handling systems have been commissioned. In addition, semiconductor wafer inspection systems, methods and techniques have historically utilized at least one of brightfield illumination, darkfield illumination and spatial filtering techniques.

With brightfield imaging, small particles on the semiconductor wafer scatter light away from a collecting aperture of an image capture device, thereby resulting in a reduction of returned energy to the image capture device. When the particle is small in comparison with the optical point spread function of a lens or digitalizing pixel, brightfield energy from the immediate areas surrounding the particle generally contribute a large amount of energy relative to the particle, thereby making the particle difficult to detect. In addition, the very small reduction in energy due to the small particle size is often masked by reflectivity variations from the immediate areas around the particle thereby resulting in increased occurrences of false defect detection. To overcome the above phenomena, semiconductor inspection systems have been equipped with high-end cameras with larger resolutions, which capture images of smaller surface areas of the semiconductor wafer. However, brightfield images generally have a better pixel contrast and this is advantageous for estimating size of defects and when inspecting dark defects.

Darkfield illumination and its advantages are generally well-known in the art. Darkfield imaging has been employed with several existing semiconductor wafer inspection systems. Darkfield imaging typically depends on the angle at which light rays are incident on the object to be inspected. At a low angle to a horizontal plane of the object to be inspected (for example 3 to 30 degrees), darkfield imaging typically produces a dark image except at locations where defects, such as surface particulates, imperfections and other irregularities exist. A particular use of darkfield imaging is to light up defects which sizes are smaller than the resolving power of lens used to produce a brightfield image. At a higher angle to the horizontal plane (for example 30 to 85 degrees), darkfield imaging typically produces better contrast images compared to brightfield images. A particular use of such high angle darkfield imaging enhances contrast of surface irregularities on a mirror finish or transparent object. In addition, high angle darkfield imaging enhances imaging of tilted objects.

Light reflectivity of the semiconductor wafer typically has a significant effect on quality of image obtained with each of brightfield and darkfield imaging. Both micro and macro structures present on the semiconductor wafer affect the light reflectivity of the semiconductor wafer. Generally, amount of light reflected by the semiconductor wafer is a function of the direction or angle of incident light, the viewing direction and the light reflectivity of the surface of the semiconductor wafer. The light reflectivity is in turn dependent on wavelength of the incident light and material composition of the semiconductor wafer.

It is generally difficult to control the light reflectivity of semiconductor wafers presented for inspection. This is because the semiconductor wafer may consist of several layers of material. Each layer of material may transmit different wavelengths of light differently, for example at different speeds. In addition, layers may have different light permeabilities, or even reflectivity. Accordingly, it will be apparent to a person skilled in the art that the use of light or illumination of a single wavelength or a narrow band of wavelengths typically adversely affects quality of captured images. Need for frequent modification of the single wavelength or narrow band of wavelengths requires use of multiple spatial filters or wavelength tuners, which can generally inconvenient. To alleviate such problems, it is important to use a broadband illumination (i.e. illumination of a wide range of wavelengths), for example broadband illumination of a range of wavelengths between 300 nm and 1000 nm.

Broadband illumination is important for achieving high quality images as well as for handling wafers with a wide range of surface reflectivities. In addition, defect detection capabilities of wafer inspections systems will generally be enhanced by use of multiple illumination angles, for example use of both brightfield and darkfield illuminations. Existing wafer systems in the market do not utilize illuminations at multiple angles and with a full broadband wavelength.

Currently available wafer inspection systems or equipments typically use one of the following methods for achieve multiple responses during wafer inspection:

(1) Multiple Image Capture Devices with Multiple Illuminations (MICD)

The MICD uses a plurality of image capture devices and a plurality of illuminations. The MCID is based on the principle of segmenting the wavelength spectrum into narrow bands, and allocating each segmented wavelength spectrum to individual illuminations. During design of systems employing the MICD method, each image capture device is paired with a corresponding illumination (i.e. illumination source), together with corresponding optical accessories such as a spatial filter or a specially coated beam splitter. For example, wavelength of the brightfield is limited between 400 to 600 nm using mercury arc lamp and spatial filter and the darkfield is limited between 650 to 700 nm using lasers. The MICD method experiences disadvantages, for example inferior image quality and design inflexibility. Inferior image quality is due to varying surface reflectivities of inspected wafers, combined with the use of illuminations with narrow wavelengths. Design inflexibility occurs because the modification of the wavelength of a single illumination typically requires reconfiguration of the entire optical setup of the wafer inspection system. In addition, the MICD method typically does not allow capture of illuminations with varying wavelengths by a single image capture device without comprising quality of captured images.

(2) Single Image Capture Device with Multiple Illuminations (SICD)

The SICD method uses a single image capture device for capturing multiple illuminations, either with segmented wavelengths or broadband wavelengths. However, it is not possible to obtain multiple illumination responses simultaneously while the wafer is in motion. In other words, the SICD method only allows one illumination response when the wafer is in motion. To achieve multiple illumination responses, the SICD method requires image captures while the wafer is stationary, which affects throughput of the wafer inspection system.

Semiconductor wafer inspection systems employing simultaneous, independent, on-the-fly image capture using broadband brightfield and darkfield or in general multiple illuminations and using multiple image capture devices are not presently available due to a relative lack of understanding as to actual implementation and operating advantages thereof. Existing semiconductor wafer inspection systems are employing either MICD or SICD as explained earlier. Equipments employing MICD do not use broadband and suffer from inferior image quality and inflexible system setup. On the other hand equipments using SICD experiences diminished system throughput and incapable of obtaining on-the-fly simultaneous multiple illumination responses.

An exemplary existing semiconductor wafer optical inspection system that utilizes both brightfield illumination and darkfield illuminator is disclosed in U.S. Pat. No. 5,822,055 (KLA1). An embodiment of the optical inspection system disclosed in KLA1 utilizes MICD as explained earlier. It uses multiple cameras to capture separate brightfield and darkfield images of semiconductor wafers. Captured brightfield and darkfield images are then processed separately or together for detecting defects on the semiconductor wafer. In addition, the optical inspection system of KLA1 captures brightfield and darkfield images simultaneously using separate sources of brightfield and darkfield illumination. KLA1 achieves simultaneous image capture using segmentation of illumination wavelength spectrum, narrow band illumination sources and spatial filters for enabling capture of the brightfield and darkfield images. In the KLA1-optical system, one of the cameras is configured to receive darkfield imaging using narrow band laser and spatial filter. The other camera is configured to receive rest of the wavelength spectrum using brightfield illumination and a beam splitter with special coating. Disadvantages of the optical inspection system disclosed by KLA1 include unsuitability thereof for imaging different semiconductor wafers comprising a large variation of surface reflectivities due to segmentation of the wavelength spectrum. The cameras are tightly coupled with respective illumination and there is no flexibility of combining of more than one available illumination to enhance certain wafer types. One such type is having carbon coated layer on its front side and they exhibit poor reflection characteristics at certain illumination angle, for example using brightfield alone. It requires combination of brightfield and high angle darkfield illumination to view certain defects. Accordingly, the optical inspection system of KLA1 requires a plurality of light or illumination sources and filters for performing multiple inspection passes (multiple scan which in turn affects the throughput of the system) to thereby capture multiple brightfield and darkfield images.

Additional exemplary exiting optical inspection systems utilizing both brightfield and darkfield imaging are disclosed in U.S. Pat. No. 6,826,298 (AUGTECH1) and U.S. Pat. No. 6,937,753 (AUGTECH2). Darkfield imaging of the optical inspection systems of AUGTECH1 and AUGTECH2 utilizes a plurality of lasers for low-angle darkfield imaging, and a fiber optic ring light for high-angle darkfield imaging. In addition, the optical inspection system of AUGTECH1 and AUGTECH2 uses a single camera sensor and belongs to SICD method explained earlier. Accordingly, inspection of semiconductor wafers in AUGTECH1 and AUGTECH2 is performed either by brightfield imaging or by darkfield imaging or via a combination of both brightfield imaging and darkfield imaging wherein each of the brightfield imaging and darkfield imaging is performed when the other is completed. The inspection system of AUGTECH1 and AUGTECH2 is not capable of simultaneous, on-the-fly or while wafer is in motion and independent brightfield and darkfield imaging. Accordingly, multiple passes of each semiconductor wafer is required for completing inspection thereof, resulting in lowered manufacturing throughput and increased utilization of resources.

In addition, several existing optical inspection systems utilize a golden image or a reference image for comparison with newly acquired images of semiconductor wafers. Derivation of the reference image typically requires capturing several images of known or manually selected "good" semiconductor wafers and then applying a statistical formula or technique to thereby derive the reference image. A disadvantage with the above derivation is that inaccuracies or inconsistencies in manual selection of the "good" semiconductor wafers. Optical inspection systems using such reference images typically suffer from false rejects of semiconductor wafers due to inaccurate or inconsistent reference images. With increasingly complex circuit geometry of semiconductor wafers, reliance on manual selection of "good" semiconductor wafers for deriving reference images is increasingly incompatible with increasingly high quality standards set by the semiconductor inspection industry.

Deriving a golden reference image involves many statistical techniques and calculations. Most of the statistical techniques are very general and have their own merits. State of the art of the currently available equipments uses either average or mean together with standard deviation to calculate a golden reference pixel. This method works well with known good pixels; otherwise any defect or noise pixel would interfere and affects final average or mean value of the reference pixel. Another method is to use median and it has reduced interference due to noise pixel but is not possible to eliminate the effect of noise substantially. All of the available equipments try to reduce the error by applying different kinds of statistical techniques such as mean, median among others, but they do not have any special or user friendly sequence to eliminate the error. Such special sequence certainly helps to eliminate pixels which would affect the final reference pixel value.

U.S. Pat. No. 6,324,298 (AUGTECH3) discloses a training method for creating a golden reference or reference image for use in semiconductor wafer inspection. The method disclosed in AUGTECH3 requires "Known Good Quality" or "Defect Free" wafers. Selection of such wafers is manually or user performed. Statistical formulas or techniques are then applied for deriving the reference image. As such, accurate and consistent selection of "good quality" wafers is crucial for accurate and consistent quality of semiconductor inspection. Further, AUGTECH3 uses mean and standard deviation to calculate individual pixels of the reference image and presence of any defective pixel will lead to inaccurate reference pixel. The defective pixel occurs due to foreign matter or other defects, which would confuse the statistical calculation and leads to incorrect reference pixel. It will be apparent to a person skilled in the art that the method of AUGTECH3 is open to inaccuracies, inconsistencies and errors in inspection of the semiconductor wafers.

In addition, optical inspection system disclosed in AUGTECH3 uses a flash or strobe lamp for illuminating the semiconductor wafers. It will be appreciated by a person skilled in the art that inconsistencies between different flashes or strobes may occur due to numerous factors including, but not limited to, temperature differentials, electronic inconsistencies and differential flash or strobe intensities. Such differentials and inconsistencies are inherent even with "good" semiconductor wafers. Presence of such differentials would affect the quality of golden reference image if the system had not taken care of such differentials due to flash lamp. In addition, illumination intensity and uniformity varies across the surface of the semiconductor wafer due to factors including, but not limited to planarity of the wafer, mounting and light reflectivity at different positions of the surface. Without taking into account the variations in the flash intensity and the strobing characteristics of the lamp, any reference images generated in the above-described manner may be unreliable and inaccurate when used for comparing with captured images of different positions of the semiconductor wafers.

Variations in product specifications, for example semiconductor wafer size, complexity, surface reflectivity and criteria for quality inspection, are common in the semiconductor industry. Accordingly, semiconductor wafer inspection systems and methods need to be capable of inspecting such variations in product specifications. However, existing semiconductor wafer inspection systems and methods are generally incapable of satisfactorily inspecting such variations in product specifications, especially given the increasing quality standards set by the semiconductor industry.

For example, a typical existing semiconductor wafer inspection system uses a conventional optical assembly comprising components, for example cameras, illuminators, filters, polarizers, mirrors and lens, which have fixed spatial positions. Introduction or removal of components of the optical assembly generally requires rearrangement and redesign of the entire optical assembly. Accordingly, such semiconductor wafer inspection systems have inflexible designs or configurations, and require a relatively long lead-time for modification thereof. In addition, distance between objective lens of the convention optical assembly and semiconductor wafer presented for inspection is typically too short to allow ease of introduction of fiber optics illumination with differing angles for darkfield illumination.

There are numerous other existing semiconductor wafer inspection systems and methods. However, because of current lack of technical expertise and operational know-how, existing semiconductor wafer inspection systems cannot employ simultaneous brightfield and darkfield imaging for an inspection while the wafer is in motion, while still having design and configurationally flexible. There is also a need for semiconductor wafer inspection systems and methods for enabling resource-efficient, flexible, accurate and fast inspection of semiconductor wafers. This is especially given the increasing complexity of electrical circuitry of semiconductor wafers and the increasing quality standards of the semiconductor industry.

SUMMARY

There is currently a lack of semiconductor wafer inspection systems and methods capable of employing both brightfield and darkfield imaging simultaneously and independently for performing inspection while the semiconductor wafer is in motion, while providing configurational or design flexibility. In addition, there is need for a semiconductor wafer inspection system wherein components thereof, for example illuminators, camera, objective lens, filters and mirrors, have flexible and adjustable spatial interconfigurations. Given the increasing complexity of electrical circuitry of semiconductor wafers, and the increasing quality standards set by the semiconductor industry, accuracy and consistency of semiconductor wafer inspection is increasingly critical. Derivation of golden references or reference images for comparison with captured images of semiconductor wafers currently require manual selection of "good" semiconductor wafers. Such a manual selection can result in inaccuracies and inconsistencies in the derived reference images, and therefore consequent inspection of semiconductor wafers. Accordingly, there is a need for improved training methods or processes for deriving reference images to which subsequent captured images of semiconductor wafers can be compared. The present invention seeks to address at least one of the above-described issues.

Embodiments of the present invention provide an inspection system and method for inspecting semiconductor components, including, but not limited to semiconductor wafers, dies, LED chips and solar wafers. The inspection system is designed for performing 2-Dimensional (2D) and 3-Dimensional (3D) wafer inspection. The inspection system is further designed for performing defect review.

The 2D wafer inspection is facilitated by a 2D optical module, which comprises at least two image capture devices. The 2D wafer inspection utilizes at least two different contrast illuminations for capturing images of corresponding contrast illuminations. The 2D wafer inspection is performed while the wafer is in motion, and is completed with one pass. The 3D wafer inspection is facilitated by a 3D optical module, which comprises at least one image capture device and at least one thin line illuminator. Thin line illumination supplied by the thin line illuminator, which is either laser or broadband illumination source or both, is directed at the semiconductor wafer while the semiconductor wafer is in motion for capturing 3D images of the semiconductor wafer. Defect review performed by the inspection system is facilitated by a defect review optical module.

In accordance with a first aspect of the embodiments of the present invention, there is disclosed a method for inspecting a wafer comprising performing a training process for creating reference images. The training process comprises capturing a plurality of images of a first wafer, the first wafer being of an unknown quality, each of the plurality of images of the first wafer being captured at a predetermined contrast illumination, each of the plurality of images of the first wafer comprising a plurality of pixels and determining a plurality of reference intensities for each of the plurality of pixels of each of the plurality of images of the first wafer. The training process further comprises calculating a plurality of statistical parameters for the plurality of reference intensities of each of the plurality of pixels of each of the plurality of images of the first wafer and selecting a plurality of reference images from the plurality of images of the first wafer based on the calculated plurality of statistical parameters. The method for inspecting the wafer further comprises capturing an image of a second wafer, the second wafer being of an unknown quality, selecting a first reference image from the plurality of reference images and comparing the captured image of the second wafer with the first reference image to thereby determine at least one of presence and type of defect on the second wafer.

In accordance with a second aspect of the embodiments of the present invention, there is disclosed a training method for obtaining a reference image comprising capturing a plurality of images of a first wafer, the first wafer being of an unknown quality, each of the plurality of images captured using a predetermined contrast illumination and selecting the reference image from the plurality of images captured. The reference image is for comparing with a test image of a second wafer, the second wafer being of an unknown quality.

In accordance with a third aspect of the embodiments of present invention, there is disclosed a method for inspecting a wafer comprising capturing a plurality of images of a first wafer, the first wafer being of an unknown quality, each of the plurality of images of the wafer captured using a predetermined contrast illumination, each of the plurality of images comprising a plurality of pixels. The method further comprises selecting the reference image from the plurality of images of the first wafer. In addition, the method comprises capturing an image of a second wafer, the second wafer being of an unknown quality. The method also comprises selecting a first reference image from the plurality of reference images and comparing the captured image of the second wafer with the first reference image to thereby determine at least one of presence and type of defect on the second wafer.

In accordance with a fourth aspect of the embodiments of present invention, there is disclosed a system for inspecting a wafer, the system comprising means for performing a training process for obtaining reference images. The training process comprises capturing a plurality of images of a first wafer, the first wafer being of an unknown quality, each of the plurality of images of the first wafer being captured at one of a plurality of predetermined contrast illuminations, each of the plurality of images of the first wafer comprising a plurality of pixels. The training process further comprises determining a plurality of reference intensities of each of the plurality of pixels of each of the plurality of images of the first wafer and calculating a plurality of weighted indices for the plurality of reference intensities of each of the plurality of pixels of each of the plurality of images of the first wafer. The training process also comprises selecting a plurality of reference images from the plurality of images of the first wafer based on the calculated plurality of weighted indices. The system for inspecting the wafer further comprises means for capturing an image of a second wafer, the second wafer being of an unknown quality, means for selecting a first reference image from the plurality of reference images, and means for comparing the captured image of the second wafer with the first reference image to thereby determine at least one of presence and type of defect on the second wafer.

In accordance with a fifth aspect of the embodiments of present invention, there is disclosed a program storage device readable by a machine, tangibly embodying a program of instructions executable by the machine to perform method steps for inspecting a wafer. The method steps for inspecting the wafer comprise the steps of performing a training process for creating reference images. The training process comprises capturing a plurality of images of a first wafer, the first wafer being of an unknown quality, each of the plurality of images of the first wafer being captured at one of a plurality of predetermined contrast illuminations, each of the plurality of images of the first wafer comprising a plurality of pixels. The training process further comprises determining a plurality of reference intensities of each of the plurality of pixels of each of the plurality of images of the first wafer and calculating a plurality of weighted indices for the plurality reference intensities of each of the plurality of pixels of each of the plurality of images of the first wafer. The training process further comprises selecting a plurality of reference images from the plurality of captured images based on the calculated plurality of weighted indices. The method steps for inspecting the wafer further comprise capturing an image of a second wafer, the second wafer being of an unknown quality, selecting a first reference image from the plurality of reference images, and comparing the captured image of the second wafer with the first reference image to thereby determine at least one of presence and type of defect on the second wafer.

BRIEF DESCRIPTION OF THE DRAWINGS

Exemplary embodiments of the present invention are described hereinafter with reference to the following drawings, in which:

FIG. 20 shows a table of illumination configurations selectable by an illumination configurator of the system of FIG. 1;

FIG. 22a shows the first image captured by the first image capture device of FIG. 1;

FIG. 22b shows the second image captured by the second image capture device of FIG. 1;

FIG. 22c shows a combined first image of FIG. 22a and second image of FIG. 22b for demonstrating image offset due to the capture of the first image and the second image when the wafer is moving;

DETAILED DESCRIPTION

The inspection of semiconductor components, for example semiconductor wafers and dies, is an increasingly critical step in the manufacture or fabrication of semiconductor components. Increasing complexity of circuitry of semiconductor wafers, coupled with increasing quality standards for semiconductor wafers, has led to an increasing need for improved semiconductor wafer inspection systems and methods.

There is currently a lack of semiconductor wafer inspection systems and methods capable of employing both brightfield and darkfield imaging simultaneously for performing on-the-fly inspection of semiconductor wafers, while providing configurational or design flexibility. In addition, there is need for a semiconductor wafer inspection system wherein components thereof, for example illuminators, camera, objective lens, filters and mirrors, have flexible and adjustable spatial interconfigurations. Given the increasing complexity of electrical circuitry of semiconductor wafers, and the increasing quality standards set by the semiconductor industry, accuracy and consistency of semiconductor wafer inspection is increasingly critical. Derivation of golden references or reference images for comparison with captured images of semiconductor wafers currently require manual selection of "good" semiconductor wafers. Such a manual selection can result in inaccuracies and inconsistencies in the derived reference images, and therefore consequent inspection of semiconductor wafers. Accordingly, there is a need for improved training methods or processes for deriving reference images to which subsequent captured images of semiconductor wafers can be compared.

Embodiments of present invention provides exemplary systems and methods for inspecting semiconductor components for addressing at least one of the above-identified issues.

For purposes of brevity and clarity, the description of the embodiments of the present invention is limited hereinafter to systems and methods for inspecting semiconductor wafers. It will however be understood by a person skilled in the art that this does not preclude the embodiments of the present invention from other applications where fundamental principles prevalent among the various embodiments of the present invention such as operational, functional or performance characteristics are required. For example, the systems and methods provided by the embodiments of the present invention can be used for inspecting other semiconductor components including, but not limited to semiconductor dies, LED chips and solar wafers.

Figure 1:
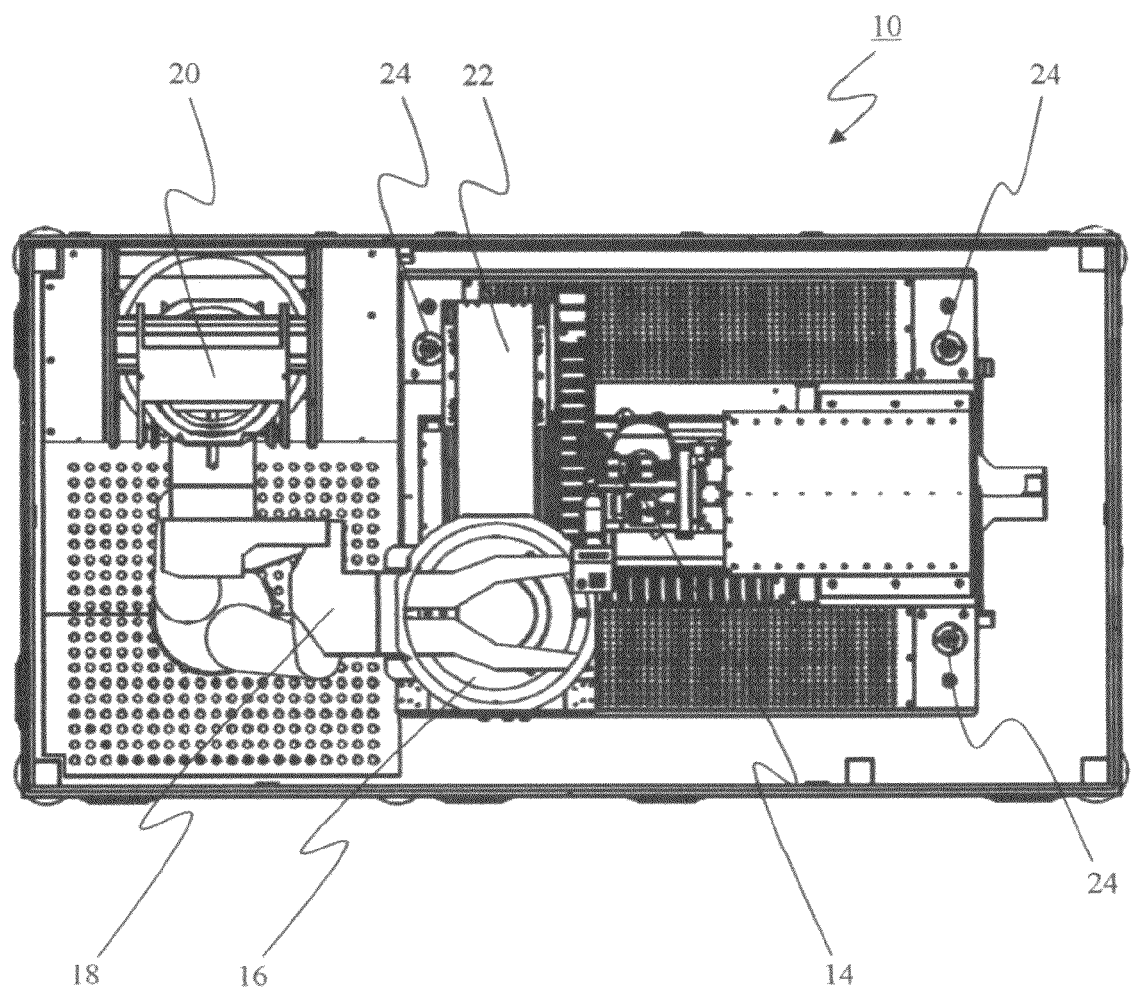
FIG. 1 shows a partial plan view of an exemplary system for inspecting wafers according to an exemplary embodiment of the present invention.
Figure 2:
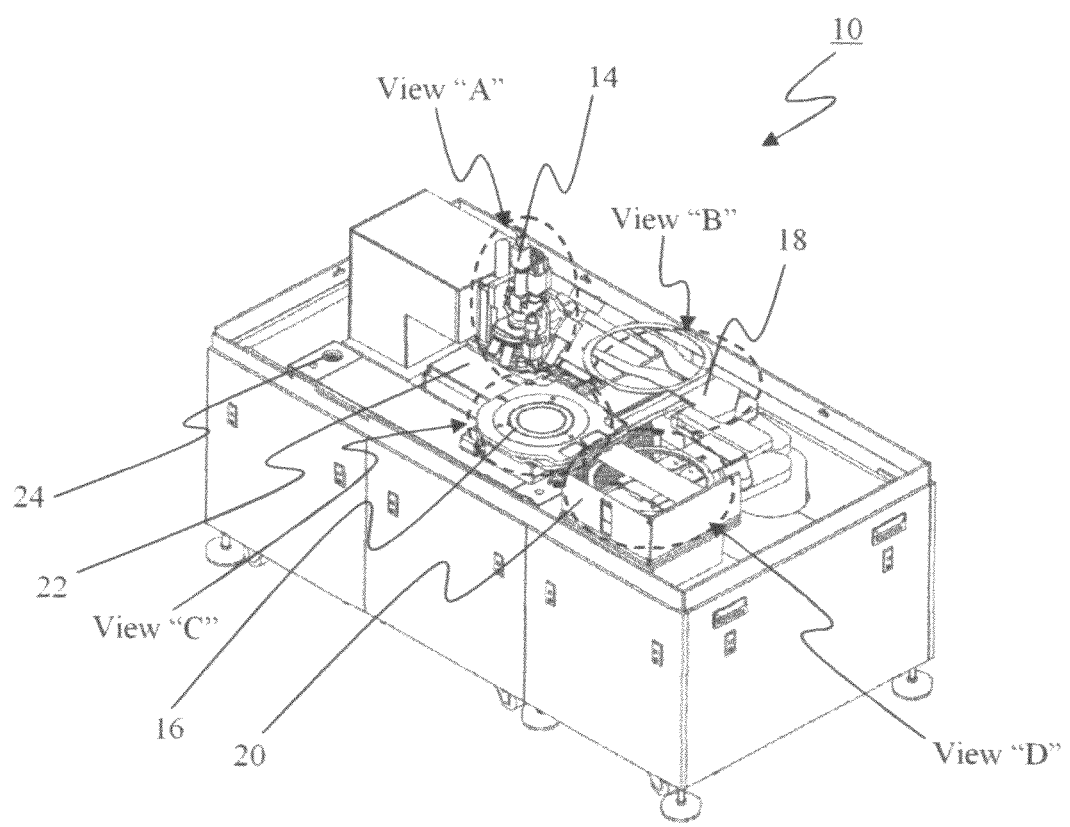
FIG. 2 shows a partial isometric view of the system of FIG. 1.
Figure 3:
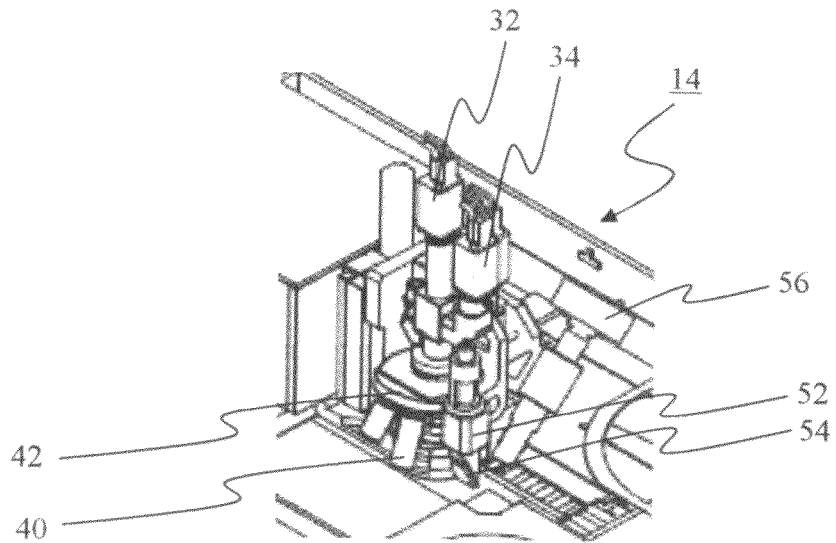
FIG. 3 shows an exploded partial isometric view of an optical inspection head of the system of FIG. 1 according to view "A" highlighted in FIG. 2.
Figure 4:
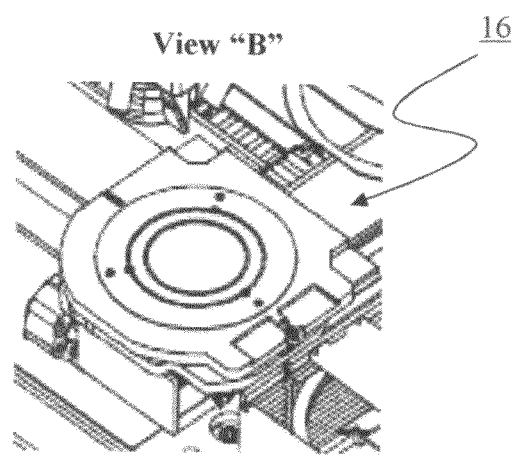
FIG. 4 shows an exploded partial isometric view of a robotic wafer table of the system of FIG. 1 according to view "B" highlighted in FIG. 2.
Figure 5:
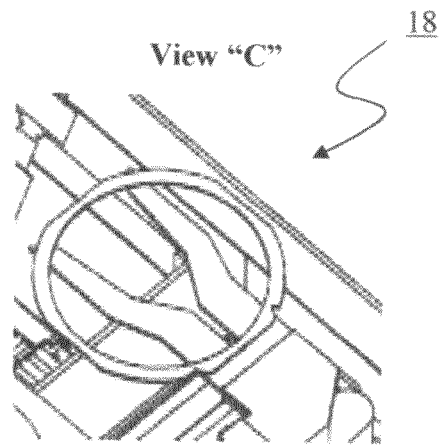
FIG. 5 shows an exploded partial isometric view of a robotic wafer loader/unloader of the system of FIG. 1 according to view "C" highlighted in FIG. 2.
Figure 6:
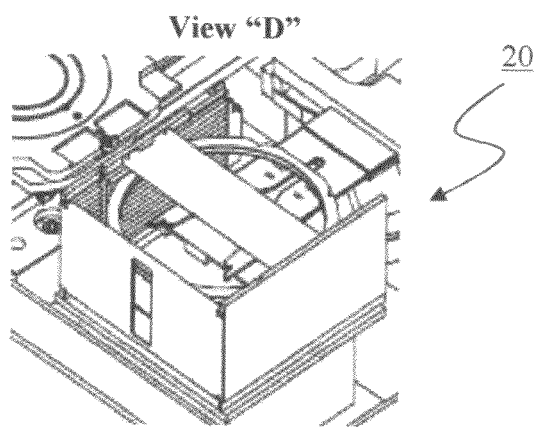
FIG. 6 shows an exploded partial isometric view of a wafer stack module of the system of FIG. 1 according to view "D" highlighted in FIG. 2.

An exemplary system 10 for inspecting semiconductor wafers 12 (also known as wafers) as shown in FIG. 1 and FIG. 2 is provided according to a first embodiment of the present invention. The system 10 can also be used for inspecting other semiconductor devices or components as required. Preferably, the system 10 comprises an optical inspection head 14 (as shown in FIG. 3), a wafer transportation table or wafer chuck 16 (as shown in FIG. 4), a robotic wafer handler 18 (as shown in FIG. 5), a wafer stack module 20 (as shown in FIG. 6) or film frame cassette holder, an XY-displacement table 22, and at least one set of quad vibration isolators 24 (as shown in FIG. 1 and FIG. 2).

Figure 7:
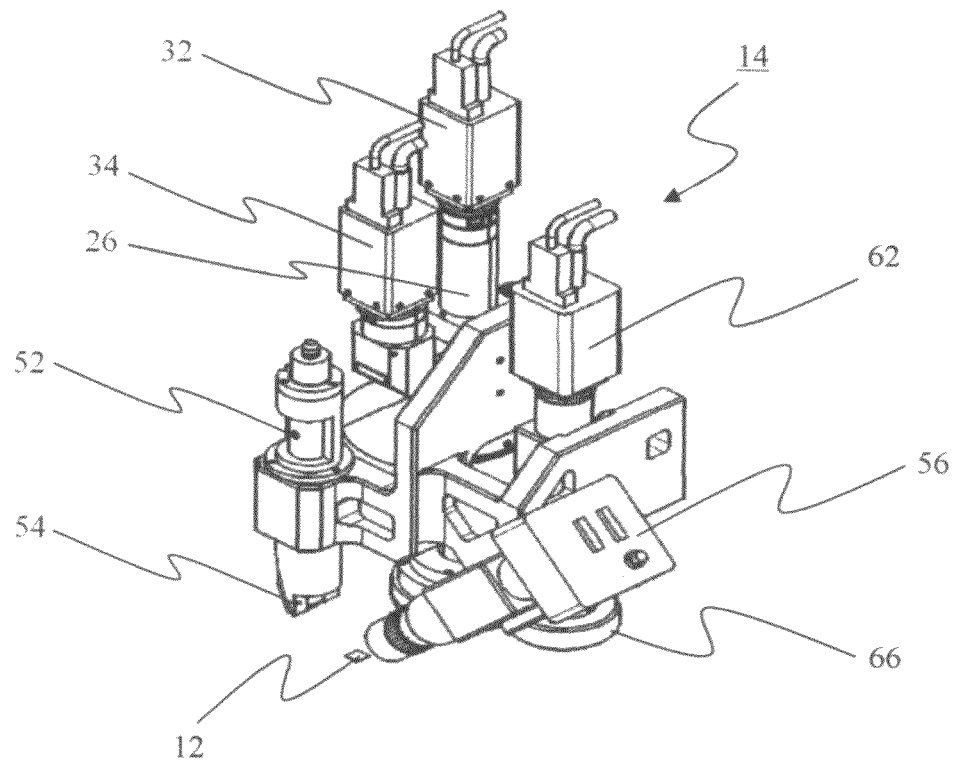
FIG. 7 shows a partial isometric view of the optical inspection head of the system of FIG. 1.
Figure 8:
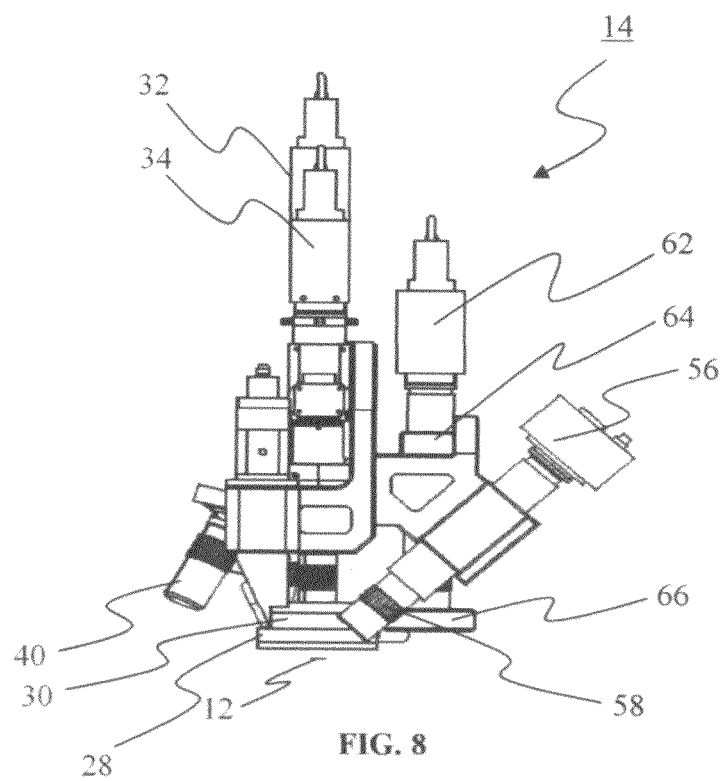
FIG. 8 shows a partial front view of the optical inspection head of the system of FIG. 1.

The optical inspection head 14 as shown in FIG. 7 and FIG. 8 comprises a number of illuminators and image capture devices. Preferably, the optical inspection head 14 comprises a brightfield illuminator 26, a low angle darkfield illuminator 28 and a high angle darkfield illuminator 30. It will be understood by a person skilled in the art that additional darkfield illuminators may be incorporated into the system 10 as required. It will be further understood by a person skilled in the art that the low angle darkfield illuminator 28 and the high angle darkfield illuminator 30 may be integrated as a single darkfield illuminator, which may be flexibly positioned as required.

The brightfield illuminator 26, also known as a brightfield illumination source or a brightfield illumination emitter, supplies or emits brightfield illumination or light. The brightfield illuminator 26 is for example, a flash lamp or a white light emitting diode. Preferably, the brightfield illuminator 26 supplies broadband brightfield illumination comprising wavelengths of substantially between and including 300 nm and 1000 nm. It will however be understood by a person skilled in the art that the brightfield illumination may be of alternative wavelengths and optical properties.

The brightfield illuminator 26 preferably comprises a first optical fiber (not shown) through which the brightfield illumination travels before being emitted from the brightfield illuminator 26. Preferably, the first optical fiber acts as a waveguide for guiding direction of travel of brightfield illumination. Further preferably, the first optical fiber facilitates directing of the brightfield illumination emitted from the brightfield illuminator 26.

The low angle darkfield illuminator 28 and the high angle darkfield illuminator 30 are also known as darkfield illumination sources, and emits or supplies darkfield illumination. Darkfield illuminators are carefully aligned illumination or light sources which enable minimization of the quantity of directly transmitted (or un-scattered) light entering their corresponding image capture devices. Generally, image capture devices for capturing darkfield images receives only illumination or light that has been scattered by a sample or object. Darkfield images generally have enhanced image contrast as compared to brightfield images. Brightfield illumination and darkfield illumination are examples of contrast illuminations.

The low angle darkfield illuminator 28 and the high angle darkfield illuminator 30 are for example flash lamps or white light emitting diodes. Preferably, the darkfield illumination supplied by each of the low angle darkfield illuminator 28 and the high angle darkfield illuminator 30 is of substantially similar optical properties as the brightfield illumination. More specifically, the darkfield illumination supplied by each of the low angle darkfield illuminator 28 and the high angle darkfield illuminator 30 is preferably a broadband darkfield illumination comprising a wavelength of substantially between and including 300 nm to 1000 nm. Alternatively, the low angle darkfield illuminator 28 and the high angle darkfield illuminator 30 supply darkfield illumination of different wavelengths or other optical properties The low angle darkfield illuminator 28 is at a lower angle, as compared to the high angle darkfield illuminator 30, to a horizontal plane of the semiconductor wafer 12 placed on the wafer table 16 (or to a horizontal plane of the wafer table 16). For example, the low angle darkfield illuminator 28 is preferably positioned at an angle of between three and thirty degrees to the horizontal plane of the semiconductor wafer 12 placed on the wafer table 16. In addition, the high angle darkfield illuminator 30 is preferably positioned at an angle of between thirty and eighty-five degrees to a horizontal plane of the semiconductor wafer 12 placed on the wafer table 16. The above-stated angles are preferably alterable as required by adjusting the position of each of the low angle darkfield illuminator 28 and the high angle darkfield illuminator 30.

Each of the low angle darkfield illuminator 28 and the high angle darkfield illuminator 30 preferably comprises a second and third optical fiber (not shown) through which the darkfield illumination travels before being emitted therefrom. Both the second and third optical fibers acts as a waveguide for guiding direction of travel of the darkfield illumination through each of the low angle darkfield illuminator 28 and the high angle darkfield illuminator 30. In addition, the second optical fiber facilitates directing of the darkfield illumination emitted from the low angle darkfield illuminator 28 and the third optical fiber facilitates directing of the darkfield illumination emitted from the high angle darkfield illuminator 30. Illumination supplied by each of the brightfield illuminator 26, the low angle darkfield illuminator 28 and the high angle darkfield illuminator 30 can be controlled, and can be either continuously supplied or pulsed.

The wavelength spectrums of both the brightfield illumination and darkfield illuminations preferably enhance accuracy of inspection and defect detection of the semiconductor wafers 12. Broadband illumination preferably enables identification of a wide range of semiconductor wafer defect types with varying surface reflectivities. In addition, the similar broadband wavelengths of both the brightfield illumination and the darkfield illuminations enable the inspection of the wafer 12 to be performed independent of reflective characteristics of the semiconductor wafer 12. This means that the detection of defects on the semiconductor wafer 12 will preferably not be undesirably influenced due to different sensitivities or reflectiveness or polarization of the semiconductor wafer 12 to different illumination wavelengths.

Preferably, intensities of the brightfield illumination and the darkfield illumination supplied by the brightfield illuminator 26 and the darkfield illuminators 28, 30 respectively can be selected and varied as required depending on the semiconductor wafer 12 characteristics, for example material of the semiconductor wafer 12. In addition, the intensities of each of the brightfield illumination and darkfield illuminations can be selected and varied as required for enhancing quality of images captured of the semiconductor wafer 12, and for enhancing inspection of the semiconductor wafer 12.

Figure 9:
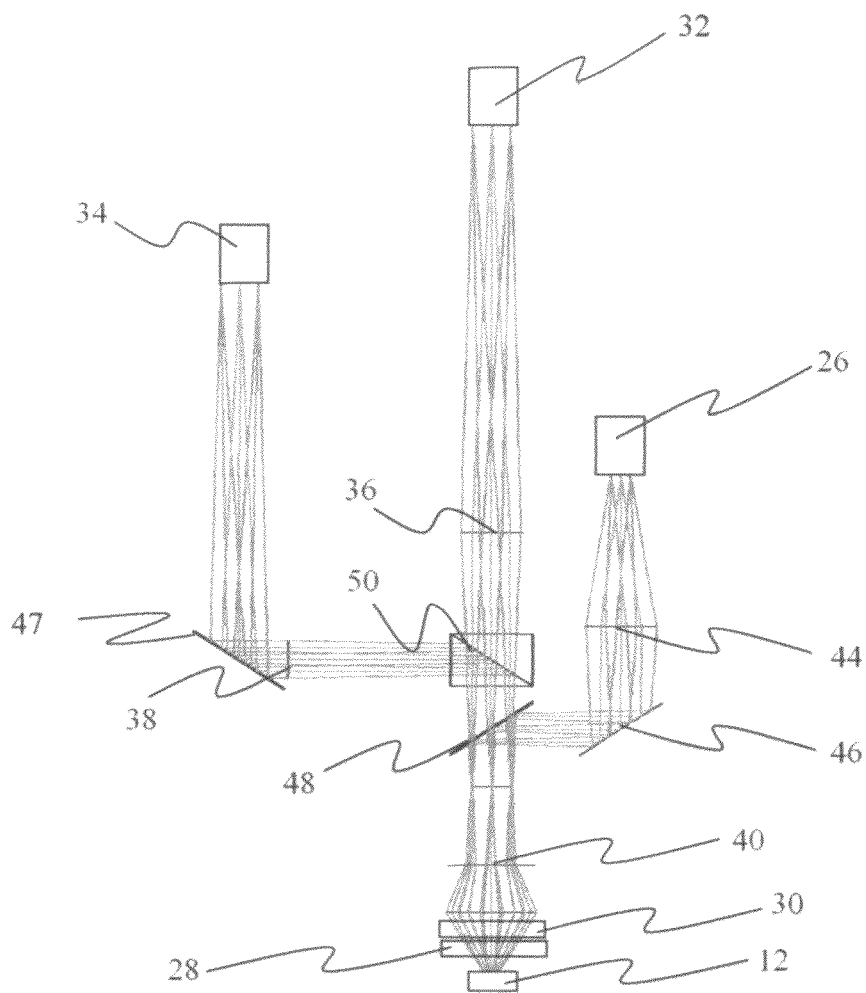
FIG. 9 shows optical ray paths of illumination between a brightfield illuminator, a low angle darkfield illuminator, a high angle darkfield illuminator, a first image capture device and a second image capture device of the system of FIG. 1.

As shown in FIG. 7 to FIG. 9, the system 10 further comprises a first image capture device 32 (i.e. a first camera) and a second image capture device 34 (i.e. a second camera). Each of the first image capture device 32 and the second image capture device 34 is capable of receiving brightfield illumination supplied by the brightfield illuminator 26 and the darkfield illuminations supplied by each of the low angle darkfield illuminator 28 and high angle darkfield illuminator 30. Brightfield and darkfield illuminations received by or entering the first image capture device 32 is preferably focused onto a first image capture plane for capture of corresponding images. Brightfield and darkfield illuminations received by or entering the second image capture device 34 is preferably focused on a second image capture plane for capture of corresponding images.

The first image capture device 32 and the second image capture device 34 capture either monochromatic or color images. Preferably, the ability to capture, using single or three chip color sensor, color images of the wafer 12 enhances at least one of accuracy and speed of defect detection. For example, the ability to capture color images of the semiconductor wafer 12 preferably helps to reduce false detection of defects on the semiconductor wafer 12, and correspondingly false rejection thereof The optical inspection head 14 further comprises a first tube lens 36 for use with the first image capture device 32. In addition, the optical inspection head 14 further comprises a second tube lens 38 for use with the second image capture device 34. Each of the first tube lens 36 and the second tube lens 38 preferably share common optical characteristics and functions. Accordingly, the tube lenses 36 and 38 have been labeled the first tube lens 36 and the second tube lens 38 solely for purposes of clarity. The optical inspection head 14 also comprises a number of objective lenses 40, for example four objective lenses 40. The objective lenses 40 are collectively mounted on a rotatable mount 42 (as shown in FIG. 3), which is rotatable for positioning each of the number of objective lens 40 above an inspection position (not shown) or semiconductor wafer 12 positioned for inspection. The objective lenses 40 may be collectively referred to as an objective lens assembly.

Each of the number objective lenses 40 is used to achieve different magnification and they are parfocal. Each of the number of objective lens 40 is preferably of a different predetermined magnification factor, for example five times, ten times, twenty times, and fifty times. Preferably, each of the number of objective lenses 40 has a corrected aberration in infinity. It will however be understood by a person skilled in the art that each of the number of objective lenses can be changed or redesigned to achieve different magnification and performance thereof.

Each of the low angle darkfield illuminator 28 and the high angle darkfield illuminator 30 preferably comprises focusing means or mechanisms for directing or focusing the darkfield illumination therefrom towards the semiconductor wafer 12 positioned at the inspection position. The angle between the low angle darkfield illuminator 28 and the horizontal plane of the wafer 12 and the angle between the high angle darkfield illuminator 30 and the horizontal plane of the wafer 12 are preferably determined and adjustable for enhancing accuracy of defect detection. Preferably, each of the low angle darkfield illuminator 28 and the high angle darkfield illuminator 30 has a fixed spatial position with reference to the inspection position. Alternatively, the position of each of the low angle darkfield illuminator 28 and the high angle darkfield illuminator 30 is variable with reference to the inspection position during normal operation of the system 10.

As described above, both the brightfield illumination and the darkfield illuminations are focused at the inspection position. The brightfield illumination and the darkfield illuminations focused at the inspection position illuminates the semiconductor wafer 12, or the portion thereof, positioned at the inspection position.

As shown in FIG. 6, the system 10 comprises a wafer stack 20 or filmframe cassette holder. The wafer stack 20 preferably comprises slots to hold multiple semiconductor wafers. Each of the semiconductor multiple wafers are sequentially loaded or transferred onto the wafer table 16 (as shown in FIG. 4) or wafer chuck by the robotic wafer handler 18 (as shown in FIG. 5). Preferably, a suction or vacuum is applied to the wafer table 16 for securing the semiconductor wafer 12 thereonto. The wafer table 16 preferably comprises a predetermined number of small holes or apertures through which vacuum is applied to enables a reliable and flat position of a flex frame tape and a frame (both not shown) onto the wafer table 16. The wafer table 16 is also preferably designed to handle wafer sizes of a range between and including six and twelve inches in diameter.

The wafer table 16 is coupled to the XY-displacement table 22 (as shown in FIG. 1 and FIG. 2), which enables the displacement of the wafer table 16 in an X- and a Y-direction. Displacement of the wafer table 16 correspondingly displaces the semiconductor wafer 12 placed thereon. Preferably, the displacement of the wafer table 16, and hence displacement of the semiconductor wafer 12 placed thereon, is controlled for controlling the positioning of the semiconductor wafer 12 at the inspection position. The XY-displacement table 22 is alternatively known as an air-gap linear positioner. The XY-displacement table 22 or air-gap linear positioner facilitates high precision displacement of the wafer table 16 in the X- and Y-directions with minimal effect of vibration transmitted from the rest of the system 10 to the wafer table 16 and ensures smooth and accurate positioning of the semiconductor wafer 12, or a portion thereof, at the inspection position. Assembly of the XY-displacement table 22 and wafer table 16 is mounted on the dampeners or vibration isolators 24 (as shown in FIG. 2) to absorb shocks or vibrations, and to ensure flatness of the assembly and other modules or accessories mounted thereon. It will be appreciated by a person skilled in the art that alternative mechanisms or devices may be coupled to or used with the wafer table 16 controlling the displacement thereof, and for facilitating high precision fine positioning of the wafer semiconductor 12 at the inspection position.

The inspection of the semiconductor wafer 12 for detecting possible defects thereon is performed while the semiconductor wafer 12 is in motion. This is to say, the capture of images, for example brightfield images and darkfield images, of the semiconductor wafer 12 preferably occurs as the semiconductor wafer 12 is being displaced across the inspection position. Alternatively, every new semiconductor wafer 12 may be stopped under the imaging means to capture high-resolution images, if the user so chooses by programming the wafer table 16 (i.e. by software control of the wafer table 16).

As previously mentioned, the system 10 further comprises the first tube lens 36 and the second tube lens 38. Preferably, the tube lens 36 is positioned between the objective lenses 40 and the first image capture device 32. Illumination passes through the first tube lens 36 before entering the first image capture device 32. Further preferably, the second tube lens 38 is positioned between the objective lenses 40 and the second image capture device 34. Illumination passes through the second tube lens 38 and deflected by a mirror or prism 47 before entering the second image capture device 34.

Each of the number of objective lenses 40 has a corrected aberration in infinity. Accordingly, after passing through the objective lens 40, illumination or light is collimated. This is to say, illumination traveling between the objective lens 40 and each of the first tube lens 36 and second tube lens 38 is collimated. The collimation of illumination between the objective lens 40 and each of the first tube lens 36 and the second tube lens 38 enhances ease and flexibility of positioning of each of the first image capture device 32 and the second image capture device 34 respectively. The implementation of the tube lenses 36, 38 also eliminates the need to refocus illuminations entering each of the first image capture device 32 and the second image capture device 34 when different objective lenses 40 are used (for example when different magnification factors are required). In addition, the collimation of illumination increases ease of introduction and positioning of additional optical components or accessories into the system 10, particularly between the objective lens 40 and each of the first tube lens 36 and the second tube lens 38. Further preferably, the collimation of illumination enables in-situ introduction and positioning of additional optical components or accessories into the system 10, particularly between the objective lens 40 and each of the first tube lens 36 and the second tube lens 38, without a need for reconfiguring the rest of the system 10. In addition, this arrangement helps to achieve longer working distance between objective lens 40 and the semiconductor wafer 12, compared to that of used in existing equipments. Longer working distances between the objective lens 40 and the wafer is necessary to use darkfield illuminations effectively.

It will therefore be appreciated by a person skilled in the art that the system 10 of the present invention allows for flexible and in-situ design and reconfiguration of components of the system 10. The system 10 of the present invention enhances ease of introduction and removal of optical components or accessories into and out of the system 10.

The first tube lens 36 facilitates focusing of collimated illumination onto the first image capture plane. Similarly, the second tube lens 38 facilitates focusing of collimated illumination onto the second image capture plane. Although, tube lenses are described for use with the system 10 in the present description, it will be appreciated by a person skilled in the art that alternative optical devices or mechanisms may be used for enabling collimation of illumination, more specifically the brighfield illumination and darkfield illuminations, and the subsequent focusing thereof onto either of the first image capture plane and the second image capture plane respectively.

The first image capture device 32 and the second image capture device 34 are preferably positioned along adjacent parallel axes. Preferably, the spatial positions of the first image capture device 32 and the second image capture device 34 are determined for reducing space occupied by the first image capture device 32 and the second image capture device 34 such that the system 10 occupies a smaller total area (i.e. is space-efficient).

Preferably, the system 10 further comprises a number of beam splitters and mirrors or reflective surfaces. The beam splitters and mirrors or reflective surfaces are preferably positioned for directing the brightfield illumination and the darkfield illuminations from each of the low angle darkfield illuminator 28 and high angle darkfield illuminator 30.

Preferably, the system 10 further comprises a central processing unit (CPU) with a storage memory or database (also known as a post processor) (not shown). The CPU is preferably electrically communicatable with or coupled to the other components of the system 10, for example the first image capture device 32 and the second image capture device 34. Images captured by the first image capture device 32 and the second image capture device 34 are preferably converted into image signals and transmitted to the CPU.

The CPU is programmable for processing information, more specifically the images, transmitted thereto to thereby detect defects present on the semiconductor wafer 12. Preferably, the detection of defects on the semiconductor wafer 12 is performed automatically by the system 10, and more specifically by the CPU. Further preferably, the inspection of semiconductor wafers 12 by the system 10 is automatic, and controlled by the CPU. Alternatively, the inspection of semiconductor wafers 12 for the detection of defects is facilitated by at least one manual input.

The CPU is programmable for storing information transmitted thereto in a database. In addition, the CPU is programmable for classifying detected defects. In addition, the CPU is preferably programmed for storing processed information, more specifically the processed images and defects detected, in the database. Further details regarding capture of images, processing of captured images, and detection of defects on the semiconductor wafers 12 are provided below.

It will be appreciated by a person skilled in the art, using the description provided above, that the brightfield illumination emitted from or supplied by the brightfield illuminator 26 and the darkfield illuminations emitted from each of the low angle darkfield illuminator 28 and the high angle darkfield illuminator 30 (hereinafter referred to as darkfield low angle or DLA illumination and darkfield high angle or DHA illumination respectively) each follows a different ray path or optical path.

Figure 10:
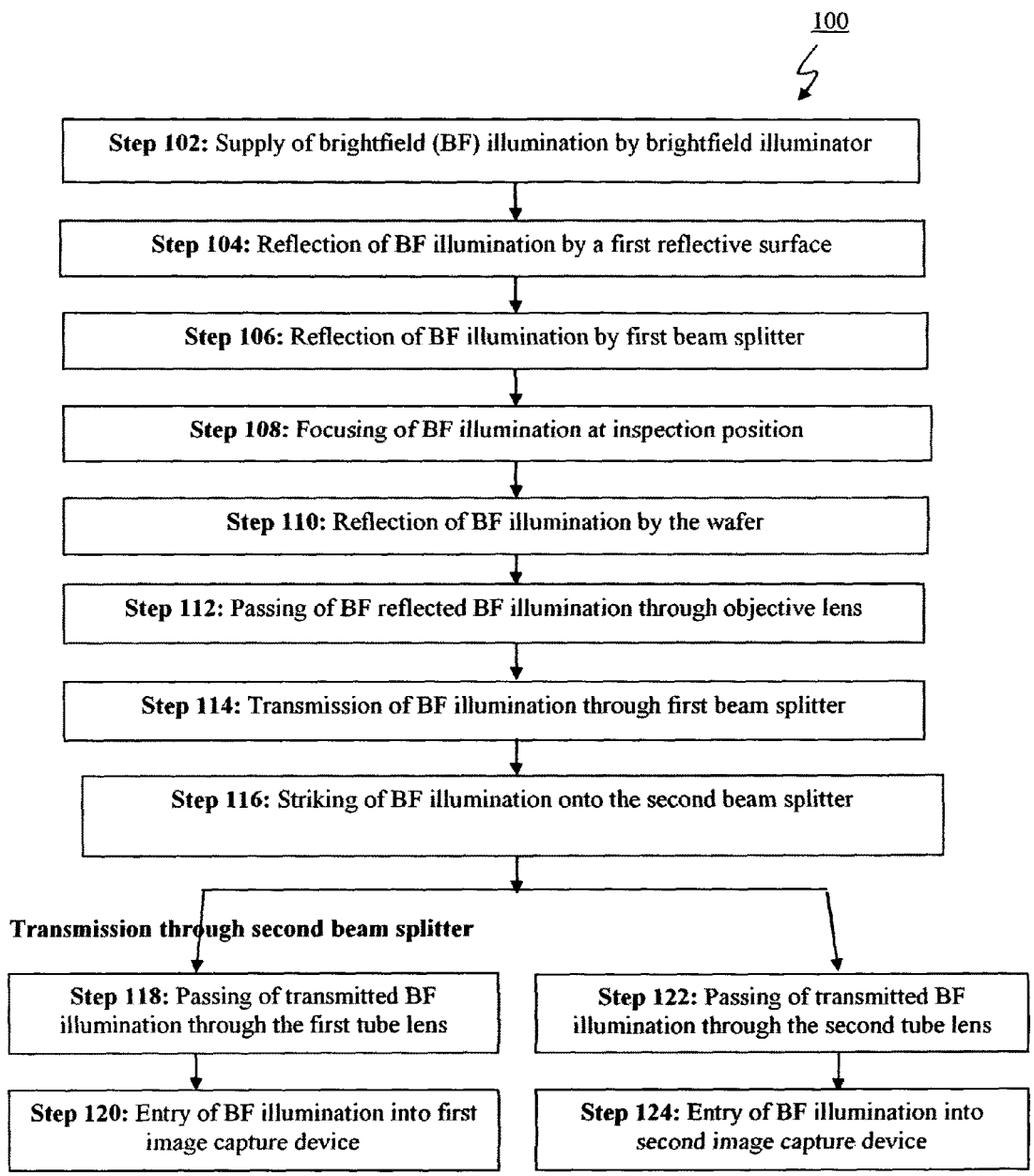
FIG. 10 is a flowchart of an exemplary first ray path followed by the brightfield illumination supplied by the brightfield illuminator of FIG. 9.

A flowchart of an exemplary first ray path 100 followed by the brightfield illumination is shown in FIG. 10.

In a step 102 of the first ray path 100, brightfield illumination or light is supplied by the brightfield illuminator 26. As previously mentioned, the brightfield illumination is preferably emitted from the first optical fiber of the brightfield illuminator 26. Preferably, the first optical fiber directs the brightfield illumination emitted from the brightfield illuminator 26. The brightfield illumination preferably passes through a condenser 44. The condenser 44 concentrates the brightfield illumination.

In a step 104, the brightfield illumination is reflected by a first reflecting surface or a first mirror. Brightfield illumination reflected by the first reflecting surface is directed towards a first beam splitter 48.

The first beam splitter 48 reflects at least a portion of the brightfield illumination striking thereonto in a step 106. Preferably, the first beam splitter 48 has a reflection/transmission (R/T) ratio of 30:70. It will however be understood by a person skilled in the art that the R/T ratio of the first beam splitter 48 can be adjusted as required for controlling the intensity or amount of brightfield illumination reflected or transmitted thereby.

The brightfield illumination reflected by the first beam splitter 48 is directed towards the inspection position. More specifically, the brightfield illumination reflected by the first beam splitter 48 is directed towards the objective lens 40 positioned directly above the inspection position. In a step 108, the brightfield illuminator 26 is focused by the objective lens 40, at the inspection position or the semiconductor wafer 12 positioned at the inspection position.

Brightfield illumination supplied by the brightfield illuminator 26, and focused at the inspection position, illuminates the semiconductor wafer 12, more specifically the portion of the semiconductor wafer 12, positioned at the inspection position. In a step 110, the brightfield illumination is reflected by the semiconductor wafer 12 positioned at the inspection position.

Brightfield illumination reflected by the semiconductor wafer 12 passes through the objective lens 40 in a step 112. As previously mentioned, the objective lens 40 has a corrected aberration in infinity. Therefore, brightfield illumination passing through the objective lens 40 is collimated by the objective lens 40. The degree of magnification of the brightfield illumination by the magnifying lens is dependent on the magnification factor of the objective lens 40.

Brightfield illumination passing through the objective lens 40 is directed towards the first beam splitter 48. In a step 114, the brightfield illumination strikes the first beam splitter 48 and a portion of thereof is transmitted through the first beam splitter 48. Extent of the brightfield illumination transmitted through the first beam splitter 48 in the step 114 depends on the R/T ratio of the first beam splitter 48. Brightfield illumination transmitted through the first beam splitter 48 travels towards a second beam splitter 50.

The second beam splitter 50 of the system 10 is preferably a cubic beam splitter 50 having a predetermined R/T ratio. Preferably the R/T ratio is 50/50. The R/T ratio may be varied as required. The cubic beam splitter 50 is preferred because the cubic bean splitter 50 splits illumination received thereby into two optical paths. It will therefore be appreciated by a person skilled in the art that the configuration and shape of the cubic beam splitter 50 will provide better performance and alignment for this purpose. Extent of illumination reflected or transmitted by the second beam splitter 50 is dependent on the R/T ratio of the second beam splitter 50. In a step 116, the brightfield illumination strikes the second beam splitter 50. The brightfield illumination striking the beam splitter is either transmitted therethrough or reflected thereby.

Brightfield illumination transmitted through the second beam splitter 50 travels towards the first image capture device 32. The brightfield illumination passes through the first tube lens 36 in a step 118 before entering the first image capture device 32 in a step 120. The first tube lens 36 helps to focus the collimated brightfield illumination onto the first image capture plane of the first image capture device 32. Brightfield illumination focused onto the first image capture plane enables capture of a brightfield image by the first image capture device 32.

The brightfield image captured by the first image capture plane is preferably converted into image signals. The image signals are subsequently transmitted or downloaded to the CPU. The transmission of image signals to the CPU is also known as data transfer. Transferred brightfield images are then at least one of processed by and stored in the CPU.

Brightfield illumination reflected by the second beam splitter 50 travels towards the second image capture device 34.

The brightfield illumination passes through the second tube lens 38 in a step 122 before entering the second image capture device 34 in a step 124. The second tube lens 38 helps to focus the collimated brightfield illumination onto the second image capture plane. Brightfield illumination focused onto the second image capture plane enables capture of a brightfield image by the second image capture device 34.

The brightfield image captured by the second image capture plane is preferably converted into image signals. The image signals are subsequently transmitted or downloaded to the CPU. The transmission of image signals to the programmable controller is also known as data transfer. Transferred brightfield images are then at least one of processed by and stored in the CPU.

Figure 11:
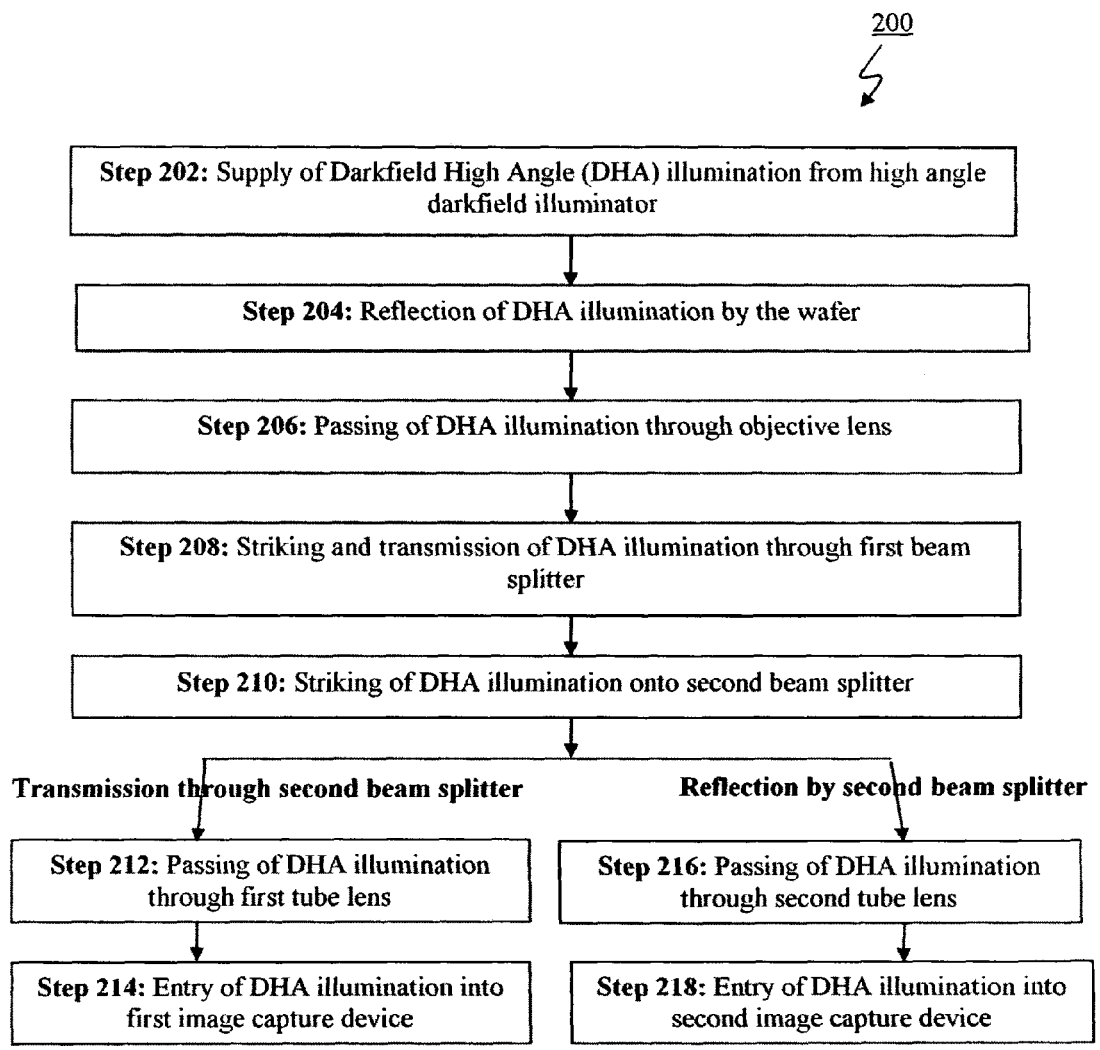
FIG. 11 is a flowchart of an exemplary second ray path followed by the darkfield high angle illumination supplied by the high angle darkfield illuminator of FIG. 9.

A flowchart of an exemplary second ray path 200 followed by the darkfield high angle (DHA) illumination is shown in FIG. 11.

In a step 202 of the second ray path 200, DHA illumination is supplied by the high angle darkfield illuminator 30. As previously mentioned, the second optical fiber preferably helps to direct the DHA illumination supplied from the high angle darkfield illuminator 30. Preferably, the DHA illumination is directly focused at the inspection position without a need to pass through optical components or accessories, for example the objective lens 40.

In a step 204, DHA illumination directed at the inspection position is reflected by the semiconductor wafer 12, or the portion thereof, positioned at the inspection position.

Reflected DHA illumination from the wafer passes through the objective lens 40 in a step 206. The objective lens 40, which has a corrected aberration in infinity, collimates the DHA illumination passing therethrough in the step 206.

DHA illumination passing through the objective lens 40 is directed towards the first beam splitter 48. In a step 208, the DHA illumination strikes the first beam splitter 48 and a portion thereof is transmitted through the first beam splitter 48. The extent of transmission of the DHA illumination through the first beam splitter 48 is dependent on the R/T ratio of the first beam splitter 48.

DHA illumination transmitted through the first beam splitter 48 is directed towards the second beam splitter 50. In a step 210, the DHA illumination strikes the second beam splitter 50. Transmission or reflection of the DHA illumination striking the second beam splitter 50 is dependent on the R/T ratio of the second beam splitter 50.

DHA illumination transmitted through the second beam splitter 50 passes through the first tube lens 36 in a step 212 before entering the first image capture device 32 in a step 214. The first tube lens 36 helps to focus the collimated DHA illumination onto the first image capture plane of the first image capture device 32. DHA illumination focused onto the first image capture plane enables capture of a darkfield image, more specifically a darkfield high angle (DHA) image by the first image capture device 32.

Alternatively, DHA illumination is reflected by the second beam splitter 50. Reflected DHA illumination, from the second beam splitter 50, passes through the second tube lens 38 in a step 216 before entering the second image capture device 34 in a step 218. The second tube lens 38 helps to focus the collimated DHA illumination onto the second image capture plane of the second image capture device 34. DHA illumination focused onto the second image capture place enables capture of a darkfield image, more specifically a darkfield high angle (DHA) image by the second image capture device 34.

Figure 12:
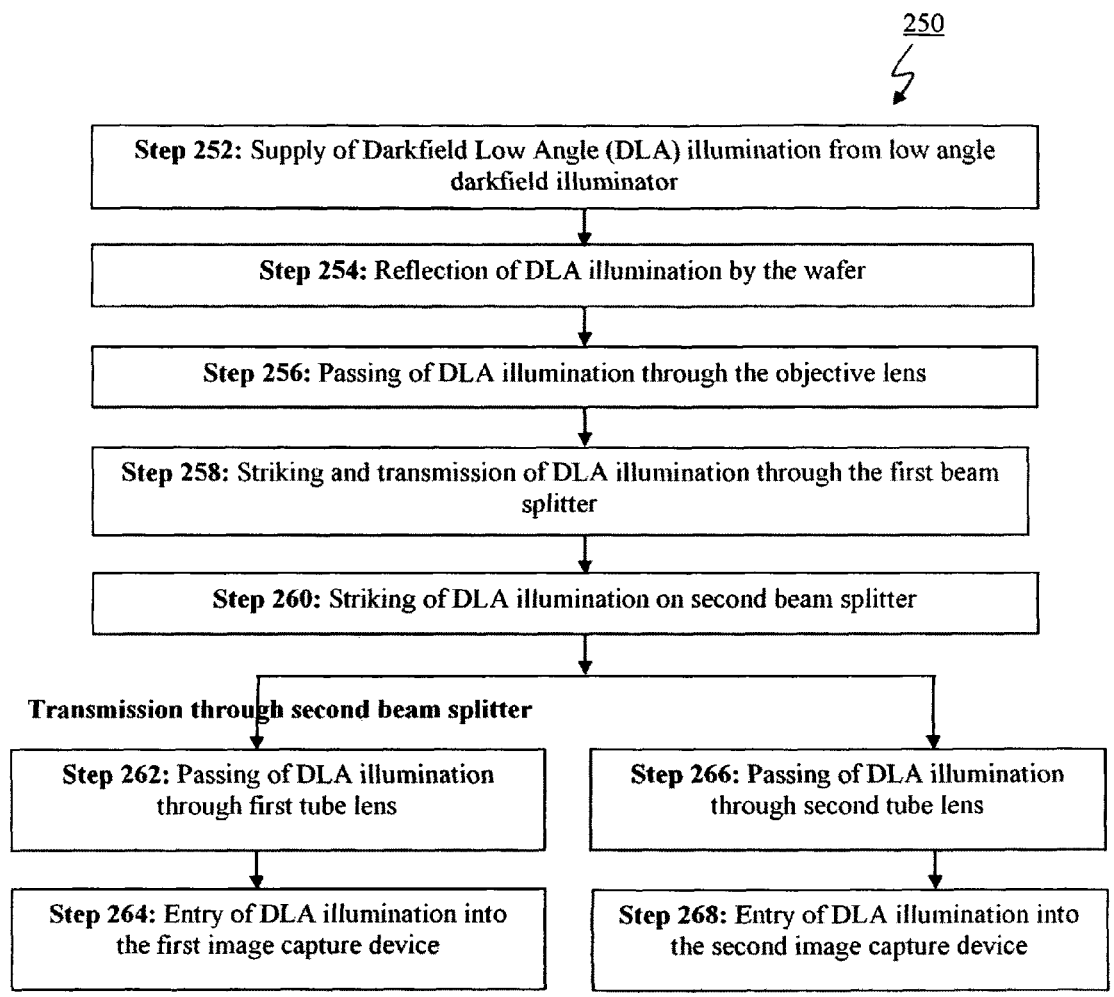
FIG. 12 is a flowchart of an exemplary third ray path followed by the darkfield low angle illumination supplied by the low angle darkfield illuminator of FIG. 9.

A flowchart of an exemplary third ray path 250 followed by the darkfield low angle (DLA) illumination is shown in FIG. 12

In a step 252 of the third ray path 200, DLA illumination is supplied by the low angle darkfield illuminator 28. The third optical fiber preferably helps to direct the DLA illumination supplied by the low angle darkfield illuminator 28. Preferably, the DLA illumination is directly focused at the inspection position without a need to pass through optical components or accessories, for example the objective lens 40.

In a step 254, DLA illumination directed at the inspection position is reflected by the semiconductor wafer 12, or the portion thereof, positioned at the inspection position. Reflected DLA illumination from the wafer passes through the objective lens 40 in a step 256. The objective lens 40, which has a corrected aberration in infinity, collimates the DLA illumination passing therethrough in the step 256.

DLA illumination passing through the objective lens 40 is directed towards the first beam splitter 48. In a step 258, the DLA illumination strikes the first beam splitter 48 and a portion thereof is transmitted through the first beam splitter 48. The extent of transmission of the DLA illumination through the first beam splitter 48 is dependent on the R/T ratio of the first beam splitter 48.

DLA illumination transmitted through the first beam splitter 48 is directed towards the second beam splitter 50. In a step 260, the DLA illumination strikes the second beam splitter 50. Transmission or reflection of the DLA illumination striking the second beam splitter 50 is dependent on the R/T ratio of the second beam splitter 50.

DLA illumination transmitted through the second beam splitter 50 passes through the first tube lens 36 in a step 262 before entering the first image capture device 32 in a step 264. The first tube lens 36 helps to focus the collimated DLA illumination onto the first image capture plane of the first image capture device 32. DLA illumination focused onto the first image capture plane enables capture of a darkfield image, more specifically a darkfield high angle (DLA) image by the first image capture device 32.

Alternatively, DLA illumination is reflected by the second beam splitter 50. Reflected DLA illumination from the second beam splitter 50, passes through the second tube lens 38 in a step 266 before entering the second image capture device 34 in a step 268. The second tube lens 38 helps to focus the collimated DLA illumination onto the second image capture plane of the second image capture device 34. DLA illumination focused onto the second image capture place enables capture of a darkfield image, more specifically a darkfield high angle (DLA) image by the second image capture device 34.

It will be appreciated by a person skilled in the art from the description provided above that the DHA illumination and DLA illumination preferably follows a similar ray path after being reflected by the semiconductor wafer 12. However, the second ray path 200 of the DHA illumination and the third ray path 250 of the DLA illumination can be individually altered as required using techniques known in the art. In addition, the angles at which the DHA illumination and the DLA illumination strike at semiconductor wafer 12 positioned at the inspection position may be adjusted as required for enhancing accuracy of defect detection. For example, the angles at which the DHA illumination and the DLA illumination strike at semiconductor wafer 12 positioned at the inspection position may be adjusted depending on type of semiconductor wafer 12 positioned at the inspection position or type of wafer defect that a user of the system 10 wishes to detect.

The DHA images and the DLA images capture by each of the first image capture device 32 and the second image capture device 34 is preferably converted into image signal, which are subsequently transmitted or downloaded to the CPU. The transmission of image signals to CPU is also known as data transfer. Transferred DHA images and DLA images can then be at least one of processed by and stored in the CPU as required.

As previously mentioned, the first image capture device 32 and the second image capture device 34 have predetermined spatial positions relative each other. The use of the objective lens 40 together with the first tube lens 36 and the second tube lens 38 facilitates the spatial positioning of the first image capture device 32 and the second image capture device 34. It will further be appreciated by a person skilled in the art that other optical components or accessories, for example mirrors, may be used for directing the brightfield illumination, DHA illumination and DLA illumination, and for facilitating the spatial positioning of the first image capture device 32 and the second image capture device 34. Preferably, the spatial positions of the first image capture device 32 and the second image capture device 34 are fixed with reference to the inspection position. The fixed spatial positions of the first image capture device 32 and the second image capture device 34 preferably enhances at least one of the accuracy and the efficiency of wafer inspection by the system 10. For example, the fixed spatial positions of the first image capture device 32 and the second image capture device 34 with respect to the inspection position preferably reduces calibration losses and adjustment feedback losses typically associated with the use of mobile image capture devices or cameras.

The optical inspection head 14 of the system 10 preferably further comprises a third illuminator (hereinafter referred to as a thin line illuminator 52). The thin line illuminator can also be referred to as a thin line illumination emitter. The thin line illuminator 52 emits or supplies thin line illumination. The thin line illuminator 52 is preferably a laser source for supplying thin line laser illumination. Alternatively, the thin line illuminator 52 is a broadband illuminator supplying a broadband thin line illumination. The thin line illumination is preferably directed at the inspection position, more specifically at the semiconductor wafer 12 positioned at the inspection position, at a predetermined angle, which can be varied as required. A mirror setup 54 or mirror is preferably coupled to, or positioned at a predetermined position relative to, the thin line illuminator 52 for directing the thin line illumination at the inspection position.

Figure 13:
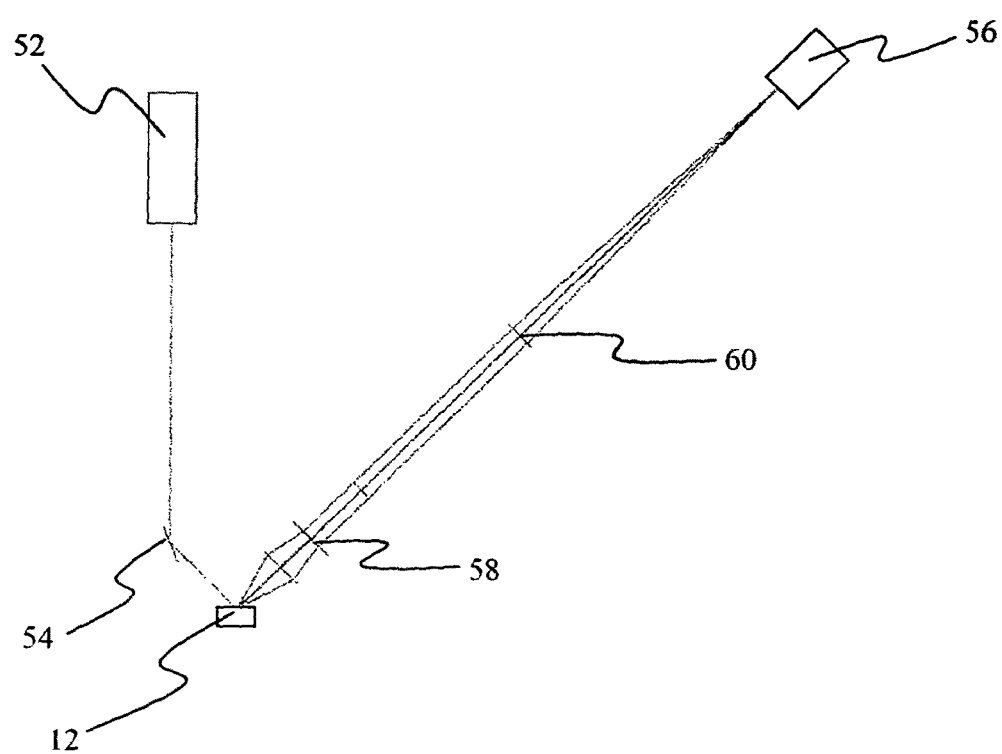
FIG. 13 shows ray path of illumination between a thin line illuminator and a 3D image capture device or camera of the system of FIG. 1.

The optical inspection head 14 of the system 10 preferably comprises a third image capture device (hereinafter referred to as a three-dimensional (3D) profile camera 56). Preferably, the 3D profile camera 56 receives the thin line illumination reflected by the semiconductor wafer 12. Preferably, the thin line illumination entering the 3D profile camera 56 is focused onto a 3D image capture plane (not shown) to thereby capture 3D images of the semiconductor wafer 12. The 3D optical setup comprising the thin line illuminator 52 and the 3D profile camera 56 is shown in FIG. 13.

The optical inspection head 14 further comprises an objective lens for the 3D profile camera 56 (hereinafter referred to as a 3D profile objective lens 58). The thin line illumination reflected by the semiconductor wafer 12 passes through the 3D profile objective lens 58 before entering the 3D profile camera 56. Preferably, the 3D profile objective lens 58 has a corrected aberration in infinity. Accordingly, the thin line illumination passing through the 3D profile objective lens 58 is collimated thereby. The optical inspection head 14 further comprises a tube lens 60 for use with the 3D profile objective lens 58 and the 3D profile camera 56. The tube lens 60 enables focusing of the collimated thin line illumination onto the 3D image capture plane. The use of the tube lens 60 with the 3D profile objective lens 58 and the 3D profile camera 56 facilitates flexible positioning and reconfiguration of the 3D profile camera 56. In addition, the use of the tube lens 60 with the 3D profile objective lens 58 and the 3D profile camera 56 enables ease of introducing additional optical components or accessories between the 3D profile objective lens 58 and the tube lens 60.

The thin line illuminator 52 and the 3D profile camera 56 preferably operate cooperatively for facilitating 3D profile scanning and inspection of the semiconductor wafer 12. Preferably, the thin line illuminator 52 and the 3D profile camera 56 are coupled to the CPU, which helps to coordinate or synchronize the operation of the thin line illuminator 52 and the 3D profile camera 56. Further preferably, an automated 3D profile scanning and inspection of the semiconductor wafer 12 is performed by the system 10. This automated 3D profile scanning and inspection of the semiconductor wafer 12 is preferably controlled by the CPU.

In addition, the optical inspection head 14 comprises a review image capture device 62. The review image capture device 62 is for example a color camera. The review image capture device 62 preferably captures color images. Alternatively, the review image capture device 62 captures monochromatic images. The review image capture device 62 preferably captures review images of the semiconductor wafer 12 for at least one of confirming, classifying and reviewing defect detected on the semiconductor wafer 12.

The optical inspection head 14 further comprises a review brightfield illuminator 62 and a review darkfield illuminator 64 for supplying brightfield illumination and darkfield illumination respectively. The review image capture device 60 receives the brightfield illumination and the darkfield illumination supplied by the review brightfield illuminator 62 and the review darkfield illuminator 64 respectively, and reflected by the semiconductor wafer 12, for capturing review images of the semiconductor wafer 12. Alternatively, the review image capture device 60 captures illumination supplied by alternative illuminators, for example one of that described above, for capturing review images of the semiconductor wafer 12. The review image capture device 60 preferably captures high-resolution images of the semiconductor wafer 12.

Figure 14:
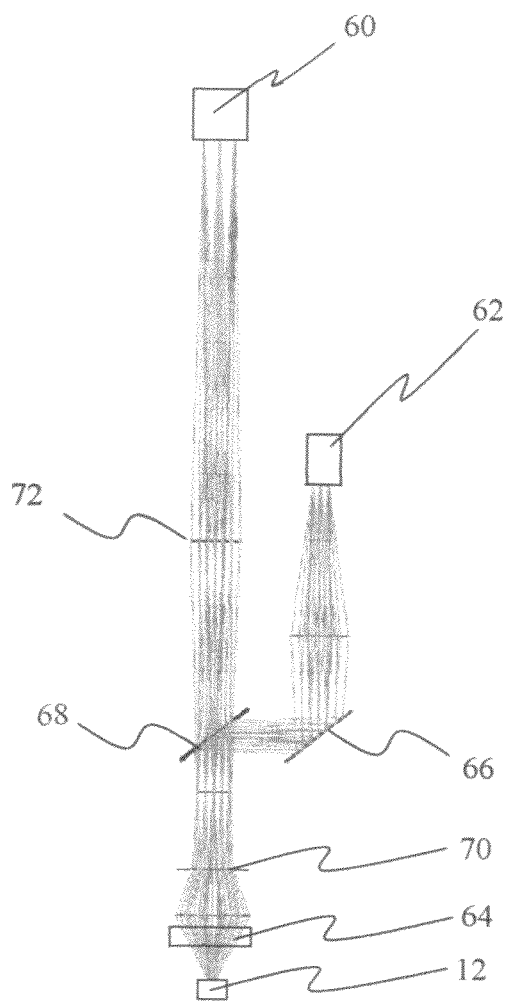
FIG. 14 shows optical ray path of illumination between a review brightfield illuminator, a review darkfield illuminator and a review image capture device of the system of FIG. 1.
Figure 15:
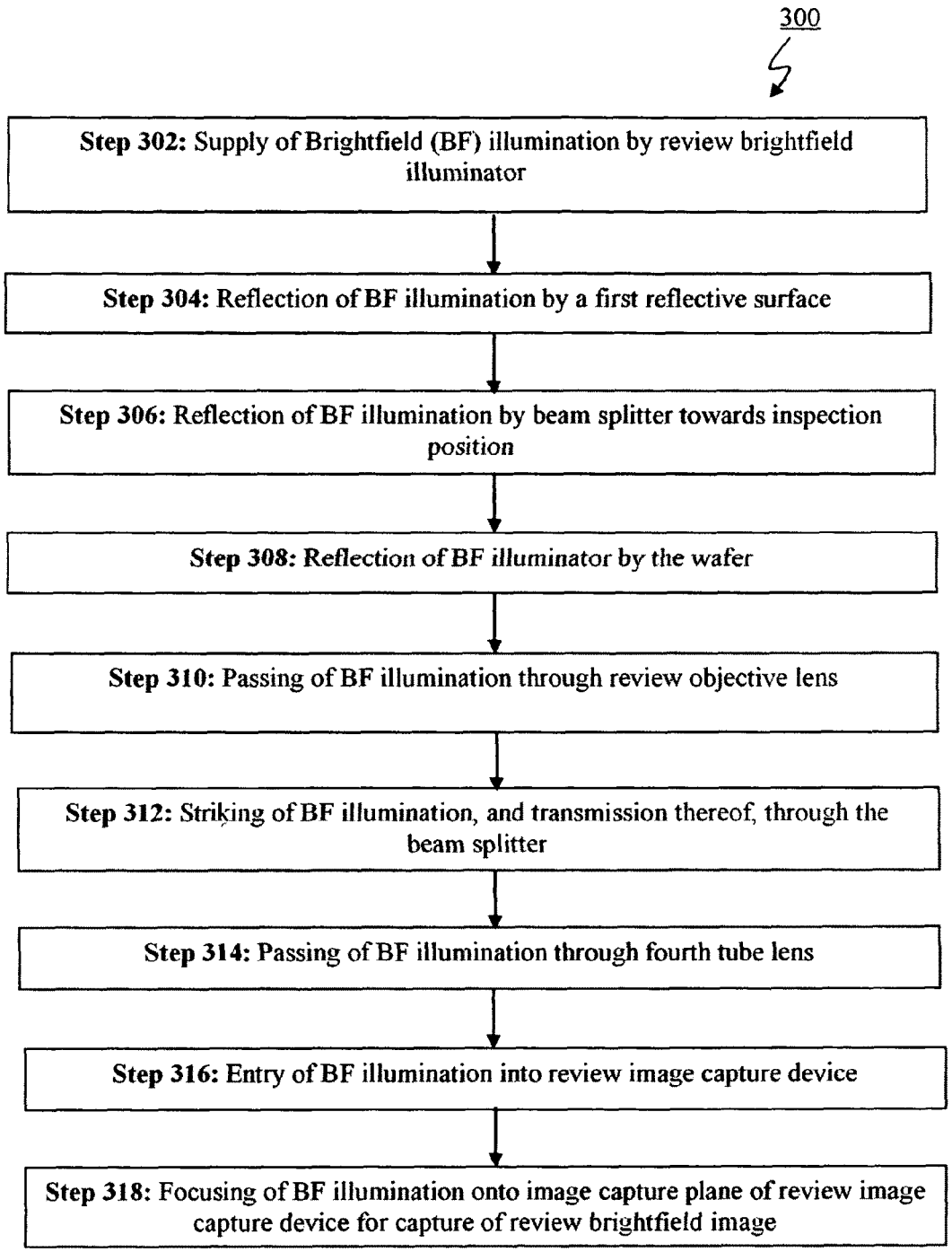
FIG. 15 is a flowchart of an exemplary fourth ray path followed by brightfield illumination between the review brightfield illuminator and the review image capture device of FIG. 14.

A diagram of showing the review brightfield illuminator 62, the review darkfield illuminator 64, the review image capture device 60 and illumination patterns therebetween, is provided in FIG. 14. A flowchart of an exemplary fourth ray path 300 followed by the brightfield illumination supplied by the review brightfield illuminator 62 is shown in FIG. 15.

In a step 302 of the fourth ray path 300, brightfield illumination is supplied by the review brightfield illuminator 62. The brightfield illumination supplied by the review brightfield illuminator 62 is directed at a first reflective surface 66. In a step 304, the brightfield illumination is reflected by the first reflective surface 66 and directed towards a beam splitter 68. In a subsequent step 306, the brightfield illumination striking the beam splitter 68 is reflected thereby and directed towards the inspection position. Extent of brightfield illumination reflected by the beam splitter 68 depends on R/T ratio thereof.

In a step 308, the brightfield illumination is reflected by the semiconductor wafer 12, or portion thereof, positioned at the inspection position. The reflected brightfield illumination passes through a review objective lens 70 in a step 310. Preferably, the review objective lens 70 has a corrected aberration in infinity. Accordingly, the brightfield illumination passing through the review objective lens 70 in the step 310 is collimated by the review objective lens 70.

In a step 312, the brightfield illumination strikes the beam splitter 68 and a portion thereof is transmitted therethrough. Extent of the brightfield illumination passing through the beam splitter 68 is depending on the R/T ratio of the beam splitter 68. The brightfield illumination then passes through a review tube lens 72 in a step 314 before entering the review image capture device 60 in a step 316. The review tube lens 72 focuses the collimated brightfield illumination onto an image capture plane of the review image capture device 60. Brightfield illumination focused on the image capture plane of the review image capture device 60 facilitates capture of review brightfield images in a step 318.

The collimation of the brightfield illumination between the review objective lens 70 and the review tube lens 72 preferably facilitates ease of introduction of optical components and accessories therebetween. In addition, the collimation of the brightfield illumination between the review objective lens 70 and the review tube lens 72 preferably enables flexible positioning and reconfiguration as required of the review image capture device 60.

Figure 16:
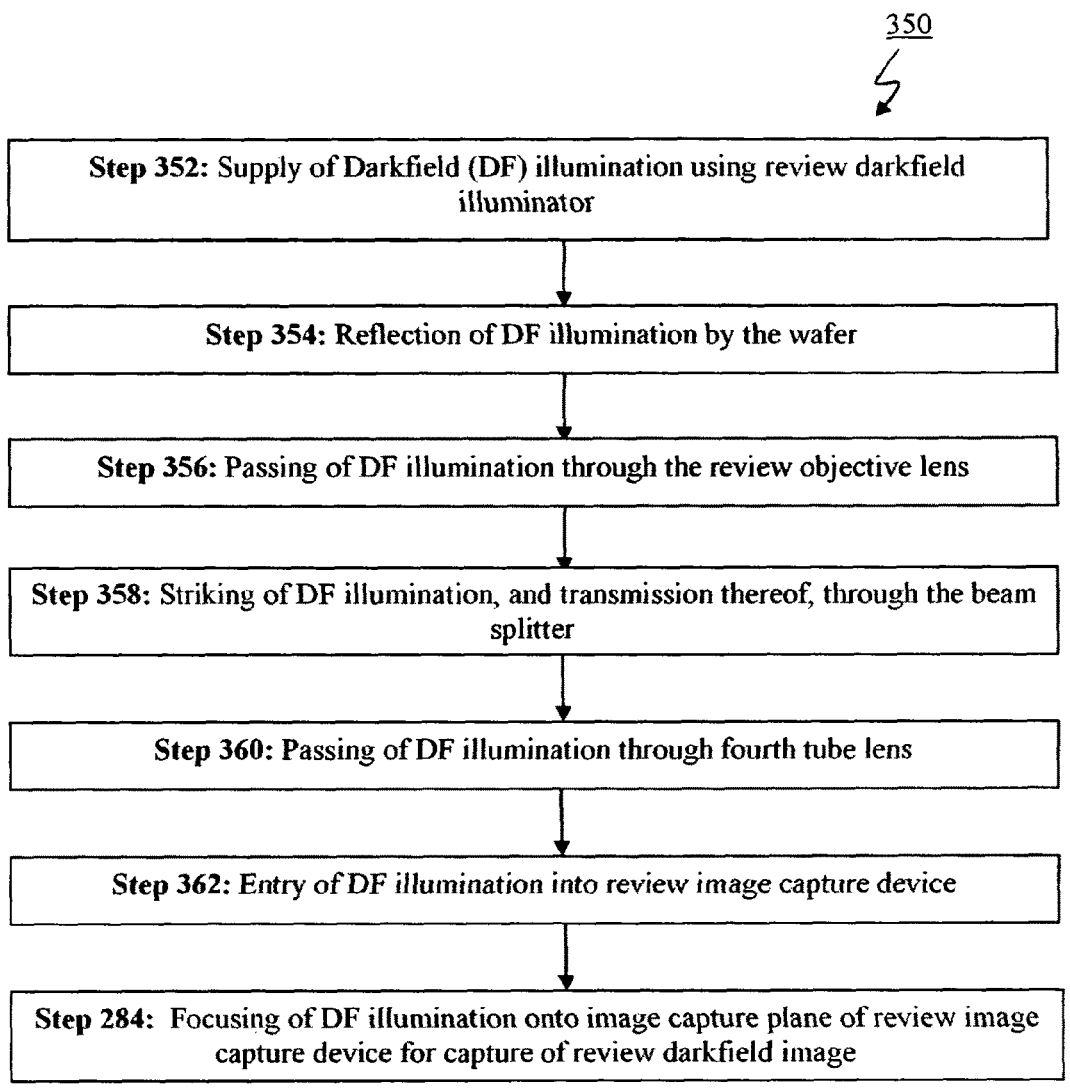
FIG. 16 is a flowchart of an exemplary fifth ray path followed by darkfield illumination between the review darkfield illuminator and the review image capture device of FIG. 14.

A flowchart of an exemplary fifth ray path 350 followed by the darkfield illumination supplied by the review darkfield illuminator 64 is shown in FIG. 16.

In a step 352 of the fifth ray path 350, darkfield illumination is supplied by the review darkfield illuminator 64. The darkfield illumination supplied by the review darkfield illuminator 64 is preferably directly focused at the inspection position. In addition, the darkfield illumination supplied by the review darkfield illuminator 64 is preferably directed at the inspection position at a predetermined angle to a horizontal plane of the semiconductor wafer 12. This predetermined angle is preferably a high angle, and can be adjusted as required using techniques known to a person skilled in the art.

In a step 354, the darkfield illumination is reflected by the semiconductor wafer 12, or portion thereof, positioned at the inspection position. The reflected darkfield illumination then passes through the review objective lens 70 in a step 356. The darkfield illumination passing through the review objective lens 70 in the step 356 is collimated by the review objective lens 70.

In a step 358, the collimated darkfield illumination strikes the beam splitter and a portion thereof is transmitted therethrough. Extent of the darkfield illumination passing through the beam splitter 68 is depending on the R/T ratio of the beam splitter 68. The darkfield illumination then passes through the review tube lens 72 in a step 360 before entering the review image capture device 60 in a step 362. The fourth tube lens 72 focuses the collimated darkfield illumination onto an image capture plane of the review image capture device 60. Darkfield illumination focused on the image capture plane of the review image capture device 60 facilitates capture of review darkfield images in a step 364. The collimation of each of the brightfield illumination and darkfield illumination between the review objective lens 70 and the review tube lens 72 enhances ease of design and configuration of the system 10. More specifically, the collimation of each of the brightfield illumination and darkfield illumination between the review objective lens 70 and the review tube lens 72 enhances ease of positioning or configuration of the review image capture device 60 with the other components of the system 10, thereby facilitating capture, while the semiconductor wafer 12 is in motion, of the review brightfield images and review darkfield images.

Captured review brightfield images and captured review darkfield images are preferably converted into image signals and transmitted from the review image capture device 60 to the programmable controller where they can be processed, and stored or saved in the database.

The review image capture device 60 can have a fixed spatial position relative the inspection position. The fixed spatial position of the review image capture device 60 preferably reduces calibration losses and adjustment feedback losses typically associated with the use of mobile image capture devices or cameras, (Note: The preceding statement is to highlight advantage of fixed position of review image capture device, made possible by use of tube lens) thereby enhancing quality of review brightfield images and review darkfield images captured.

The system 10 further comprises vibration isolators 24, which are collectively known as a stabilizer mechanism. The system 10 is preferably mounted on the vibration isolators 24 or stabilizer mechanism when the system is in normal operation. Preferably the system 10 comprises four vibration isolators 24, each positioned at a different corner of the system 10. The vibration isolators 24 help to support and stabilize the system 10. Each vibration isolator 24 is preferably a compressible structure or canister, which absorbs ground vibrations to thereby serve as a buffer for preventing transmission of ground vibrations to the system 10. By preventing unwanted vibrations or physical movements to the system 10, the vibration isolators 24 help to enhance quality of images captured by each of the first image capture device 32, the second image capture device 34, the 3D profile camera 56 and the review camera 60, and to thereby improve quality of inspection of the semiconductor wafer 12.

Figure 17A:
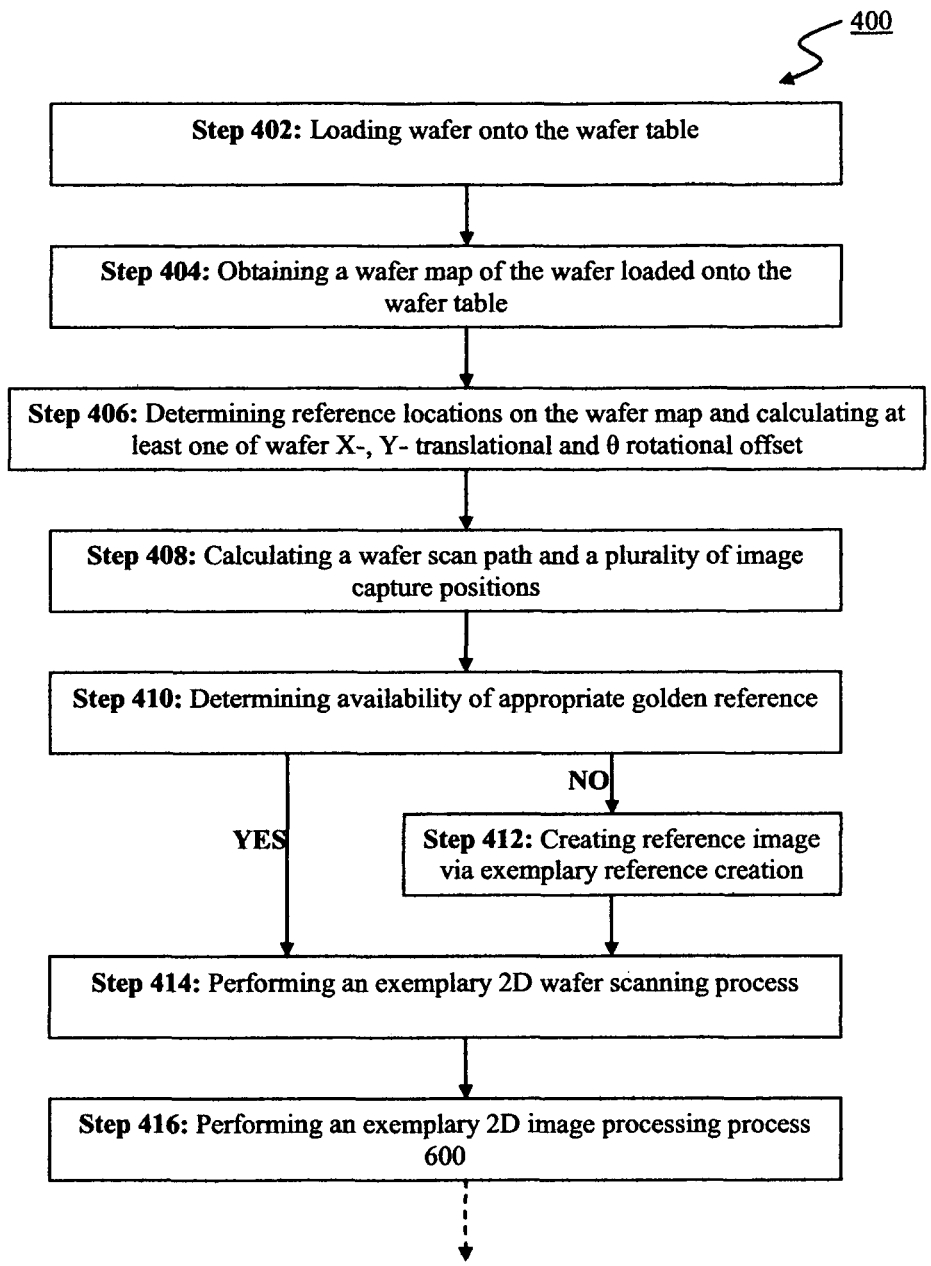
FIGS. 17A and 17B are a method flow diagram of an exemplary method for inspecting wafers provided by the present invention.
Figure 17B:
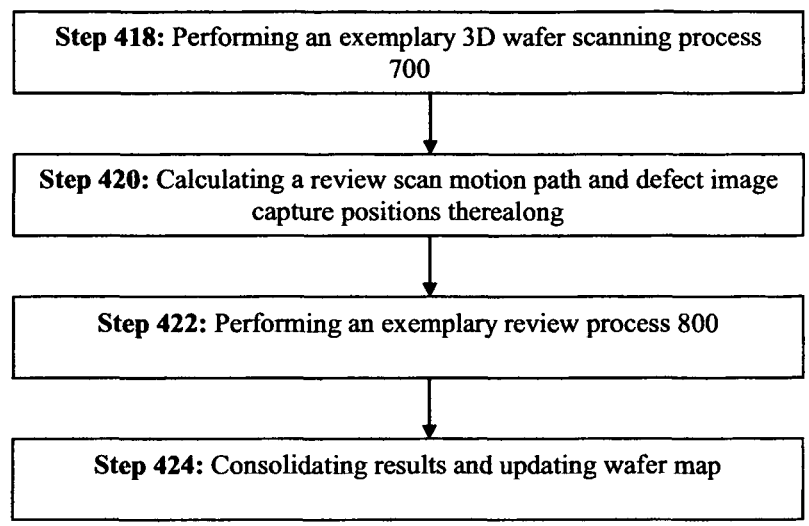

An exemplary method 400 for inspecting the semiconductor wafer 12 is provided according to an embodiment of the present invention. A method flow diagram of the exemplary method 400 is shown in FIGS. 17A and 17B. The method 400 for inspecting the semiconductor wafer 12 enables at least one of detection, classification and review of defects on the semiconductor wafer 12.

Figure 18A:
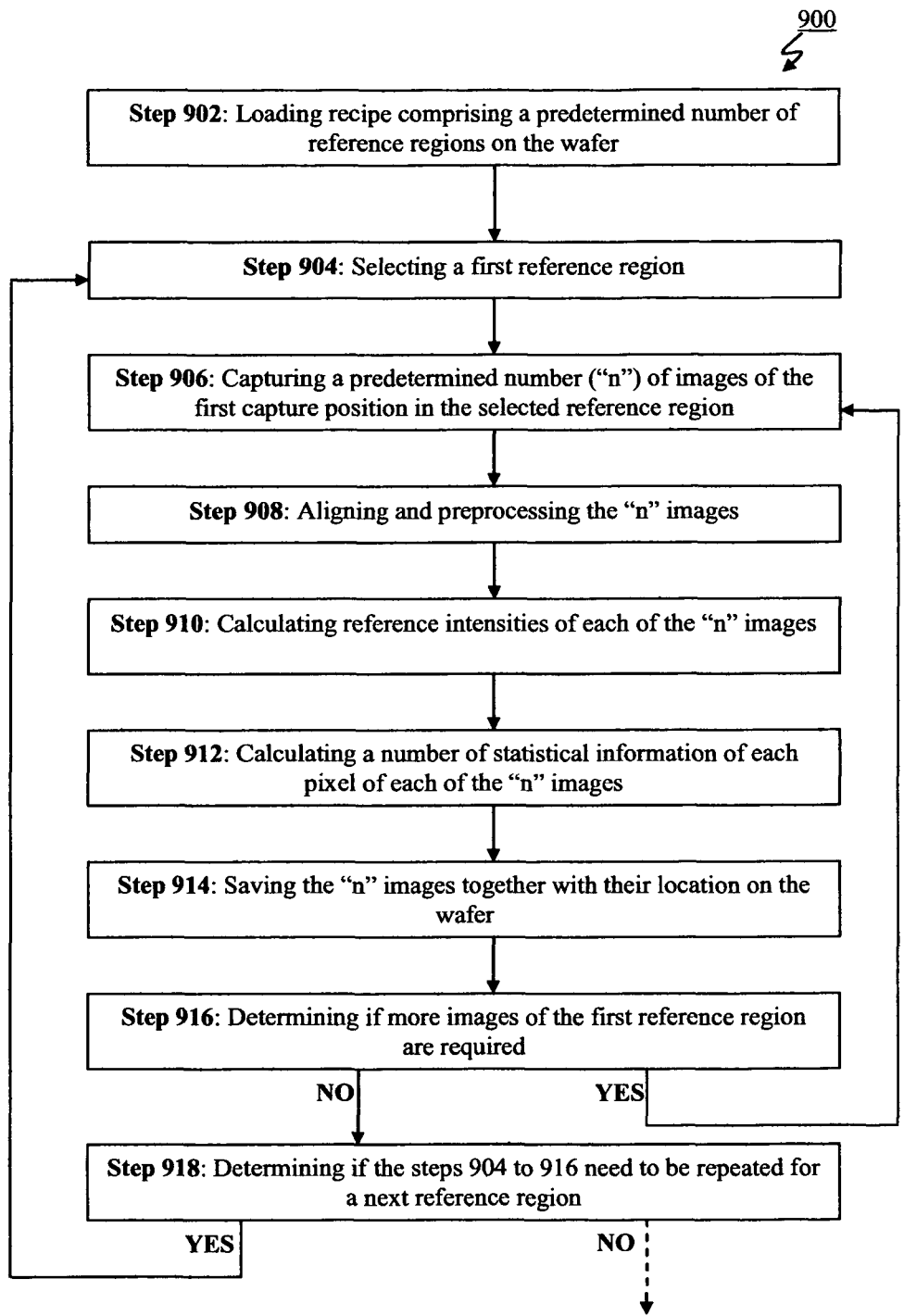
FIGS. 18A and 18B are a process flowchart of an exemplary reference image creation process for creating reference images used for comparing with images captured during performance of the method of FIGS. 17A and 17B.
Figure 18B:
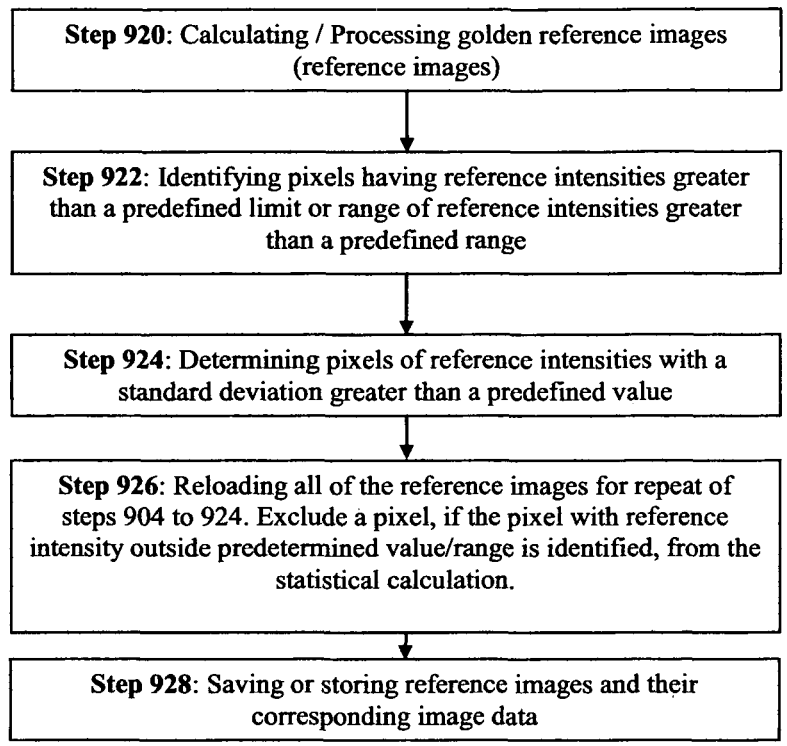

The exemplary method 400 for inspecting semiconductor wafers 12 utilizes reference images (also known as golden references) to which captured images of the semiconductor wafers 12 are compared for at least one of detecting, classifying and review of defects on the semiconductor wafers 12. For purposes of clarity, description of an exemplary reference image creation process 900 is provided before the description of the exemplary method 400. The exemplary reference image creation process 900 is shown in FIGS. 18A and 18B.

Exemplary Reference Image Creation Process 900

In a step 902 of the reference image creation process 900, a recipe comprising a predetermined number of reference regions on the semiconductor wafer 12 is loaded. The recipe is preferably created or derived by a computer software program. Alternatively, the recipe is manually created. The recipe can be stored in the database of the CPU. Alternatively, the recipe is stored in an external database or memory space.

Each of the predetermined reference regions represents locations on the semiconductor wafer 12, which is of an unknown quality. The use of multiple reference regions helps to compensate for possibility of surface variations at different locations on the semiconductor wafer 12, or between multiple wafers. Such surface variations include, but are not limited to, differential planarity and illumination reflectivity. It will be understood by a person skilled in the art that the predetermined number of reference regions may represent an entire surface area of the semiconductor wafer 12. Alternatively, the predetermined number of reference regions may represent multiple predetermined locations on multiple wafers.

In a step 904, a first reference region is selected. In a subsequent step 906, a predetermined number ("n") of images are captured of the first capture position of the selected reference region. More specifically, the n images are captured at each predetermined locations of the selected reference region. Number and location of the predetermined locations of the selected reference region can be varied as required and facilitated by at least one of software program and manual input.

The n images can be captured using at least one of the first image capture device 32, the second image capture device 34 and the review image capture device 62 as required. Alternatively, the n images are captured using a different image capture device. Illuminations used for capture of the n images can be varied as required, and are for example one or combination of the brightfield illumination, the DHA illumination and the DLA illumination. Colors and intensities of the illuminations used for capture of the n images can be selected, and varied, as required.

Capture of multiple images at each position preferably enables reference images to be created taking into account the variations in the illumination, optical setup and the imaging means used during capture of the reference images. This method of reference image creation minimizes unwanted influences or effects on defect detection, and classification, due to variations between the illumination conditions. In addition, a number of images of the selected reference region may be captured for each specified illumination condition. Preferably, capture of multiple images at each specified illumination condition facilitates a normalizing or compensation of illumination variation from flash to flash or from strobe to strobe.

The n images are preferably stored in the database of the CPU. Alternatively, the n images are stored in an external database or memory space as required. In a step 908, the n images captured in the step 906 are aligned and preprocessed. Preferably, subpixels of the n images captured in the step 906 are registered. Registration of the subpixels of the n images is preferably performed using known references including, but not limited to, traces, bumps or pads formed on the one or more wafer using one or more of binary, grey scale or geometrical pattern matching.

In a step 910, reference intensities of each of the n images are calculated. More specifically, reference intensity of each image captured at each of the predetermined locations of the selected reference region is calculated. Preferably, the calculation of reference intensities of each of the n images helps to normalize or compensate for color variation at different locations or regions on the semiconductor wafer 12 (or the multiple wafers). Further preferably, the calculation of reference intensities of each of the n images helps to account, or compensate, for other surface variations at different locations or regions on the semiconductor wafer 12 (or the multiple wafers).

The step 910 results in calculated of n reference intensities, each of the n reference intensities corresponding to one of the n images. In a step 912, a number of statistical information of intensities each pixel of each of the n images are calculated. The number of statistical information includes, but is not limited to, an average, a range, a standard deviation, a maximum and a minimum intensity for each pixel of each of the n images.

More specifically, the average is a geometric mean of the reference intensity for each pixel of each of the n images. Geometric mean is a type of mean or average, which indicates the central tendency or typical value of a set of numbers, or n numbers. The numbers of the set are multiplied and then the nth root of the resulting product is obtained. A formula for obtaining geometric mean is shown below:

$$\left( \prod_{i=1}^{n} a_i \right)^{1/n} = \sqrt[n]{a_1 \cdot a_2 \ldots a_n}$$

Calculation of the geometric mean instead of arithmetic mean or median prevents the average intensity calculated for each pixel of each of the n images from being unduly affected by extreme values in a data set.

In addition, range of absolute intensity (hereinafter referred to as Ri) for each pixel of the n images is calculated. Preferably, the Ri for each pixel of the n images is the value between a maximum and a minimum absolute intensity for each pixel of the n images.

As previously mentioned, the standard deviation of the intensity of each pixel for each of the n images of the first reference region captured in the step 906 is also calculated. More specifically, the standard deviation is a geometric standard deviation, which describes how spread out are a set of numbers whose preferred average is the geometric mean. A formula for obtaining the standard deviation is shown below:

$$\sigma_g = \exp\left( \sqrt{ \frac{\sum_{i=1}^{n} (\ln A_i - \ln \mu_g)^2}{n} } \right).$$

where $\mu_g$, is the geomtric mean of a set of numbers $\{A_1, A_2, \ldots, A_n\}$.

In a step 914, the n images captured are temporarily saved, together with their corresponding information such as location on the semiconductor wafer 12 or first reference region. The statistical information calculated in the step 912 is preferably also temporarily saved in the step 914. Preferably, the above data is saved in the database of the CPU. Alternatively, the above data is saved in an alternative database or memory space as required.

In a step 916, it is determined if more images of the selected reference region are required. The step 916 is preferably software controlled and preformed automatically. Preferably, the step 916 is performed with a reliance on information obtained by the steps 910 and 912. Alternatively, the step 916 is manually facilitated or controlled using techniques known in the art.

If it is determined in the step 916 that more images of the selected reference region are required, the steps 904 to 916 are repeated. The steps 904 to 916 can be repeated any number of times as required. When it is determined in the step 916 that no more images of the first reference region is required, a step 918 of determining if the steps 904 to 916 need to be repeated for a next reference region (for purposes of the present description, a second reference region) of the predetermined number of reference regions. The step 918 is preferably software controlled and performed automatically. In addition, the step 918 is preferably performed using information obtained in at least one of steps 910, 912 and 916. Alternatively, the step 918 is manually facilitated or controlled using techniques known in the art.

If it is determined in the step 918 that images of the second reference region need to be captured, i.e. if the steps 904 to 916 need to be repeated for the second reference region, a signal is generated for repeating the steps 904 to 916. The steps 904 to 918 can be repeated any number of times as required. Repetition of the steps 904 to 918 is preferably software controlled and automated.

When it is determined in the step 918 that the steps 904 to 918 do not need to be repeated, i.e. that images of the next reference region of the predetermined number of reference regions are not required, golden reference images (hereinafter referred to as reference images) are then calculated in a step 920.

The calculation of the reference images is preferably software controlled, and is performed via a series of program instructions. The following steps are exemplary steps performed for calculating the reference images. It will however be understood by a person skilled in the art that additional steps or techniques complementary to the following steps may be performed in the calculation of the reference image.

In a step 922, pixels having reference intensities greater than a predefined limit is determined. In addition, pixels having range of pixel intensities greater than a predefined range is determined in the step 922. The predefined limit and range of the step 922 can be software selected and determined or manually determined. In a step 924, pixels of intensities with a standard deviation greater than a predefined value are identified. The predefined value of the step 924 can be software selected and determined or manually determined. In a step 926, the previously saved images, as in the step 914, are reloaded for repeat of any one of more of the steps 904 to 924 if a pixel with reference intensities outside predetermined value or range is identified during the steps 922 to 924.

The steps 922 to 926 facilitate identification of images comprising pixels of specific pixel intensities. More specifically, the steps 922 to 926 enable identification of images containing pixels having reference intensities outside predefined limits or ranges, for example identification of "undesirable" images, to be identified. More specifically, the steps 922 to 926 eliminate "undesirable" pixels from the reference image calculation and help to prevent "undesirable" pixels influence on the final reference pixel values of the reference image.

The "undesirable" images are discarded. This facilitates elimination of defective data or images, thereby preventing influence or presence of such defective data with generated reference images. In a step 928, images comprising pixels within predefined limits and ranges (i.e. images not discarded) are consolidated.

Preferably, the reference image creation process 900 results in derivation of the following image data:
(a) Normalized average of intensity of each pixel of each of the consolidated images
(b) Standard deviation of intensity of each pixel of each of the consolidated images
(c) Maximum and minimum intensities of each pixel of each of the consolidated images
(d) Average reference intensity of each of the predetermined number of reference regions determined in the step 702

The consolidated images of the step 928 represent reference images. The reference images, together with corresponding image data is further saved in the step 928. The reference images and their corresponding image data are preferably saved in the database of the CPU. Alternatively, the reference images and their corresponding image data are saved in an alternative database or memory space. It will be appreciated by a person skilled in the art that the step 922 to 926 helps to reduce amount or size of memory space required for storing the reference images and their corresponding data, which may enable the method 400 to be performed at a higher speed or accuracy.

The average intensity of each pixel is preferably normalized to 255 in order to display and visualize the reference images. It will however be understood by a person skilled in the art that the average intensity of each pixel can be normalized to an alternative value in order to display and visualize the reference images.

The steps 904 to 928 can be repeated a predetermined number of times for capturing a corresponding number of images with at least one of the first image capture device 32, the second image capture device 34 and the review camera. In addition, the steps 904 to 928 can be repeated for capturing images at different illuminations or illumination conditions, for example brightfield illumination, DHA illumination, DLA illumination and thin line illumination, as required. The repetition of the steps 904 to 928 enables creation of reference images for multiple illuminations or illumination conditions, and with multiple image capture devices as required.

As previously described, the derivation of reference images for multiple reference regions of the semiconductor wafer 12 (or multiple wafer) and at multiple illumination conditions helps to ensure accountability, and compensation where required, for variations in quality of subsequently captured images due to variations in the lighting conditions. For example, the capture of reference images at different reference regions of the semiconductor wafer 12 (i.e. different locations on the semiconductor wafer 12) preferably ensures accountability and compensation for color variations at different locations on the semiconductor wafer 12.

The steps 904 to 928 are preferably executed and controlled by the CPU. Preferably, the steps 904 to 928 are at least one of executed and controlled by a software program. Alternatively, at least one of the steps 904 to 928 may be manually assisted if required. The reference images created by the exemplary reference image creation process 900 are used for comparison with subsequently captured images of semiconductor wafers 12 of unknown quality to thereby enable at least one of detection, classification and review of defects on the semiconductor wafer 12.

As previously mentioned, the present invention provides the exemplary method 400 for inspection of semiconductor wafers 12 to thereby at least one of detect, classify and review defects present on the semiconductor wafers 12.

In a step 402 of the method 400, the semiconductor wafer 12 to be inspected by the system 10 is loaded onto the wafer table 16. Preferably, the semiconductor wafer 12 is extracted from the wafer stack 20 by the robotic wafer handler 18 and transferred onto the wafer table 16. Suction or vacuum is applied to the wafer table 16 to secure the semiconductor wafer 12 thereonto.

The semiconductor wafer 12 preferably comprises a wafer identification number (ID number) or barcode. The wafer ID number or barcode is engraved or tagged onto a surface of the semiconductor wafer 12, more specifically at a periphery of the surface of the semiconductor wafer 12. The wafer ID number or barcode helps to identify the semiconductor wafer 12 and ensures that the semiconductor wafer 12 is correctly or appropriately loaded onto the wafer table 16.

In a step 404, a wafer map of the semiconductor wafer 12 loaded onto the wafer table 16 is obtained. The wafer map may be loaded from the database of the programmable controller. Alternatively, the wafer map may be retrieved from an external database or processor. Further alternatively, the wafer map may be prepared or derived upon the loading of the semiconductor wafer 12 onto the movable support platform using methods or techniques known to a person skilled in the art.

In a step 406, one or more reference locations are captured or determined on the wafer map and at least one of wafer X, Y translational and θ rotational offset is calculated using techniques known to a person skilled in the art.

In a subsequent step 408, a wafer scan motion path and a plurality of image capture positions are calculated or determined. The wafer map obtained in the step 404 preferably facilitates the calculation of the wafer scan motion path and the plurality of image capture positions. Preferably, the calculation of the wafer scan motion path is dependent on at least one of several known parameters. Such known parameters include, but are not limited to, rotation offset, wafer size, wafer die size, wafer pitch, inspection area, wafer scan velocity and encoder position. Each of the plurality of image capture positions reflects or corresponds to a position on the semiconductor wafer 12 of which images are to be captured. Preferably, each of the plurality of image capture positions can be altered as required using techniques known to a person skilled in the art. The number of image capture positions can also be altered as required using techniques known to a person skilled in the art.

Preferably, the steps 404 to 408 are performed automatically by the system 10, more specifically by the programmable controller of the system 10. Alternatively, any one of the steps 404 to 408 may be performed by, or with the aid of, an alternative processor.

In a step 410, the programmable controller of the system 10 determines availability of an appropriate golden reference (hereinafter referred to as a reference image). If the reference image is not available, the reference image is created by the exemplary reference image creation process 900 as described above in a step 412.

Figure 19:
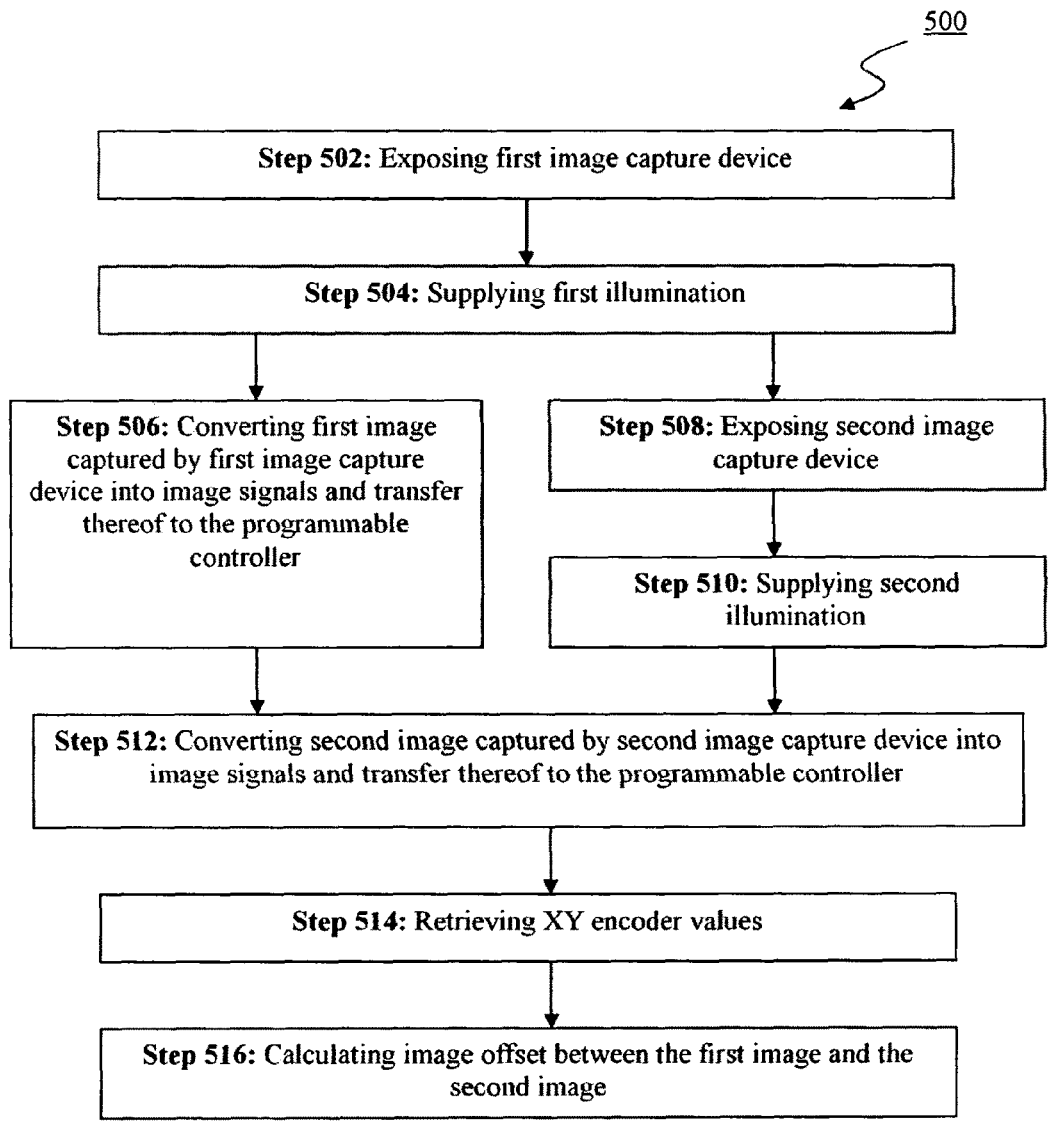
FIG. 19 is a process flow diagram of an exemplary two-dimensioned wafer scanning process with timing offset in the method step of the method of FIGS. 17A and 17B.

Preferably, the reference image is obtained, or created, before performing an exemplary two-dimensional (2D) wafer scanning process 400 in a step 414. A process flow diagram of the exemplary two-dimensional (2D) wafer scanning process 500 is shown in FIG. 19.

Exemplary Two-Dimensional (2D) Wafer Scanning Process 500

The 2D wafer scanning process 500 enables capture of brightfield images and darkfield images by the first image capture device 32 and the second image capture device 34.

In a step 502 of 2D wafer scanning process 500, the first image capture device 32 is exposed. In a step 504, a first illumination is supplied. The first illumination is for example brightfield illumination supplied by the brightfield illuminator 26, DHA illumination supplied by the high angle darkfield illuminator 30 or DLA illumination supplied by the low angle darkfield illuminator 28. Selection of the first illumination to be supplied in the step 504 is preferably determined by an illumination configurator (not shown). Preferably, the illumination configurator is a component of the system 10 and electronically coupled to the illuminators (28, 30, 52, 64 and 66) of the system 10. Alternatively, the illumination configurator is a component of the CPU.

The image capture devices 32 and 34 can use any combination of illuminations provided by brightfield illuminator 26, DHA illuminator 30 and DLA illuminator 28. Few of the possible combinations for the first illumination used by the image capture device 32 and the second illumination used by the image capture device 34 are shown in the table of FIG. 19. If the first image capture device 32 and the second image capture device 34 use substantially similar illumination then the throughput of such configuration would be the highest of all the configurations possible.

For purposes of the present description, configuration 1 as shown in the table of FIG. 20 is selected by the illumination configurator. Accordingly, the first illumination is the brightfield illumination supplied by the brightfield illuminator 26.

Preferably, the steps 502 and 504 are performed simultaneously. Performance of the steps 502 and 504 enables capture of a first image, as shown in FIG. 22a, by the first image capture device 32. In a step 506, the first image captured by the first image capture device 32 is converted into image signals and transmitted to the CPU via the data transfer process and preferably stored in the database or storage memory.

In a step 508, the second image capture device 34 is exposed. In a step 510, a second illumination is supplied. As with the first illumination, selection of the second illumination is preferably determined by the illumination configurator. For purposes of the present description, configuration 1 as shown in the table of FIG. 20 is selected by the illumination configurator. Accordingly, the second illumination is the DHA illumination supplied by the high angle darkfield illuminator 30. It will however be appreciated by a person skilled in the art that the first illumination and the second illuminations may be alternative illuminations as required, for example those of the different configurations shown in the table of FIG. 20.

Preferably, the steps 508 and 510 are performed simultaneously. Preferably, the step 506 occurs in tandem with the performance of the steps 508 and 510. Performance of the steps 508 and 510 enables capture of a second image, as shown in FIG. 22b, by the second image capture device 34. In a step 512, the second image captured by the second image capture device 34 is converted into image signals and transmitted to the programmable controller via the data transfer process and preferably stored in the database or storage memory.

Figure 21:
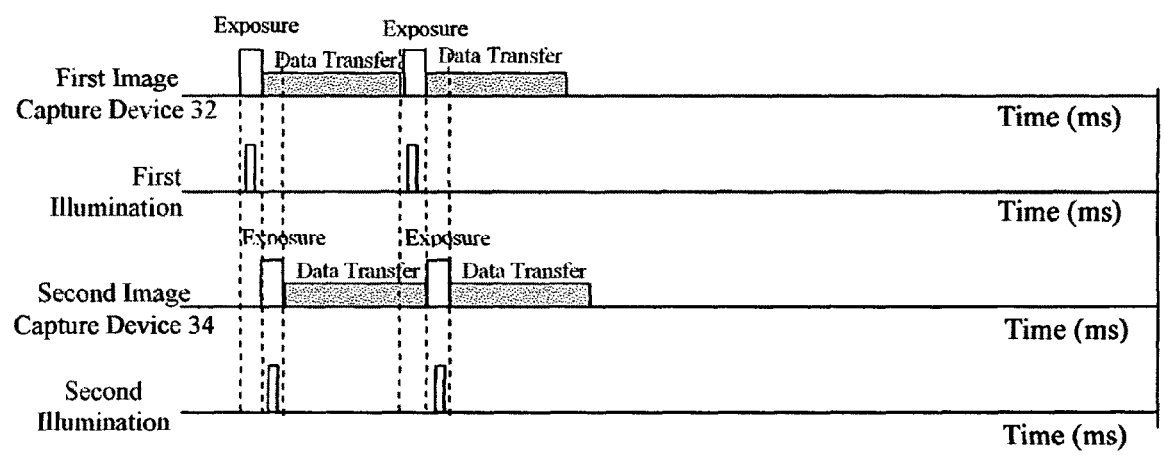
FIG. 21 shows a timing chart for capturing of a first image by the first image capture device and capturing of a second image by the second image capture device.

A diagram showing the exposure of the first image capture device 32, supply of the first illumination, exposure of the second image capture device 34, supply of the second illumination and the data transfer processes is provided by FIG. 21. The steps 502 to 512 can be repeated any number of times for capturing a corresponding number of sets of first images and second images of the semiconductor wafer 12. More specifically, the steps 502 to 512 are preferably repeated for capturing images with the first illumination and the second illumination of the semiconductor wafer 12 at each of the plurality of image capture positions along the wafer scan motion path as calculated in the step 408.

As previously described, each of the first image and the second image are converted into image signals and transmitted to the programmable controller and stored in the database or storage memory. Each of the steps 502 to 512 is performed while the semiconductor wafer 12 is in motion. This is to say, the capture of the first image and the second image is performed while the semiconductor wafer 12 is in motion along the wafer scan motion path. Accordingly, a person skilled in the art will appreciate that the semiconductor wafer 12 will be displaced by a predetermined distance along the wafer scan motion path between the steps 502, 504 (which preferably occur simultaneously) and the steps 508, 510 (which preferably also occur simultaneously). The predetermined distance depends on several factors including, but not limited to, speed of displacement of the semiconductor wafer 12 along the wafer scan motion path and time required for any one of the steps 502 to 512. The predetermined distance may be controlled and varied as required, for example by the CPU. The control and variation of the predetermined distance may be at least one of software or manually facilitated.

Accordingly, the first image will have a predetermined image offset when superimposed onto or compared with the second image. FIG. 22c shows a combined image of the first image and the second image demonstrating resulting image offset due to the capture of the first image and the second image while the semiconductor wafer 12 is in motion. The predetermined image offset depends on several factors including, but not limited to, speed of displacement of the semiconductor wafer 12 along the wafer scan motion path and time required for any one of the steps 502 to 512. Control and variation of the predetermined image offset may be at least one of software or manually facilitated.

In a step 514, XY encoder values are retrieved. The XY encoder values are preferably obtained at during each of the steps 504 and 510. Preferably, the XY encoder values represent positions (XY-displacement) of the semiconductor wafer 12 along the wafer scan motion path. The XY encoder values obtained are used for calculating the image offset (coarse offset) between the first image and the second image (i.e. relative offset of the second image from the first image) in a step 516. The fine image offset is calculated by performing sub pixel image alignment using pattern matching techniques. The final offset is obtained by applying a predetermined mathematical formula on the coarse and fine image offsets. The predetermined mathematical formula may be adjusted as required using techniques known to a person skilled in the art.

The 2D wafer scanning process 500 performed in the step 414 of the method 400 results in the capture of multiple images of the semiconductor wafer 12, preferably at the calculated image capture positions along the wafer scan motion path.

Figure 23:
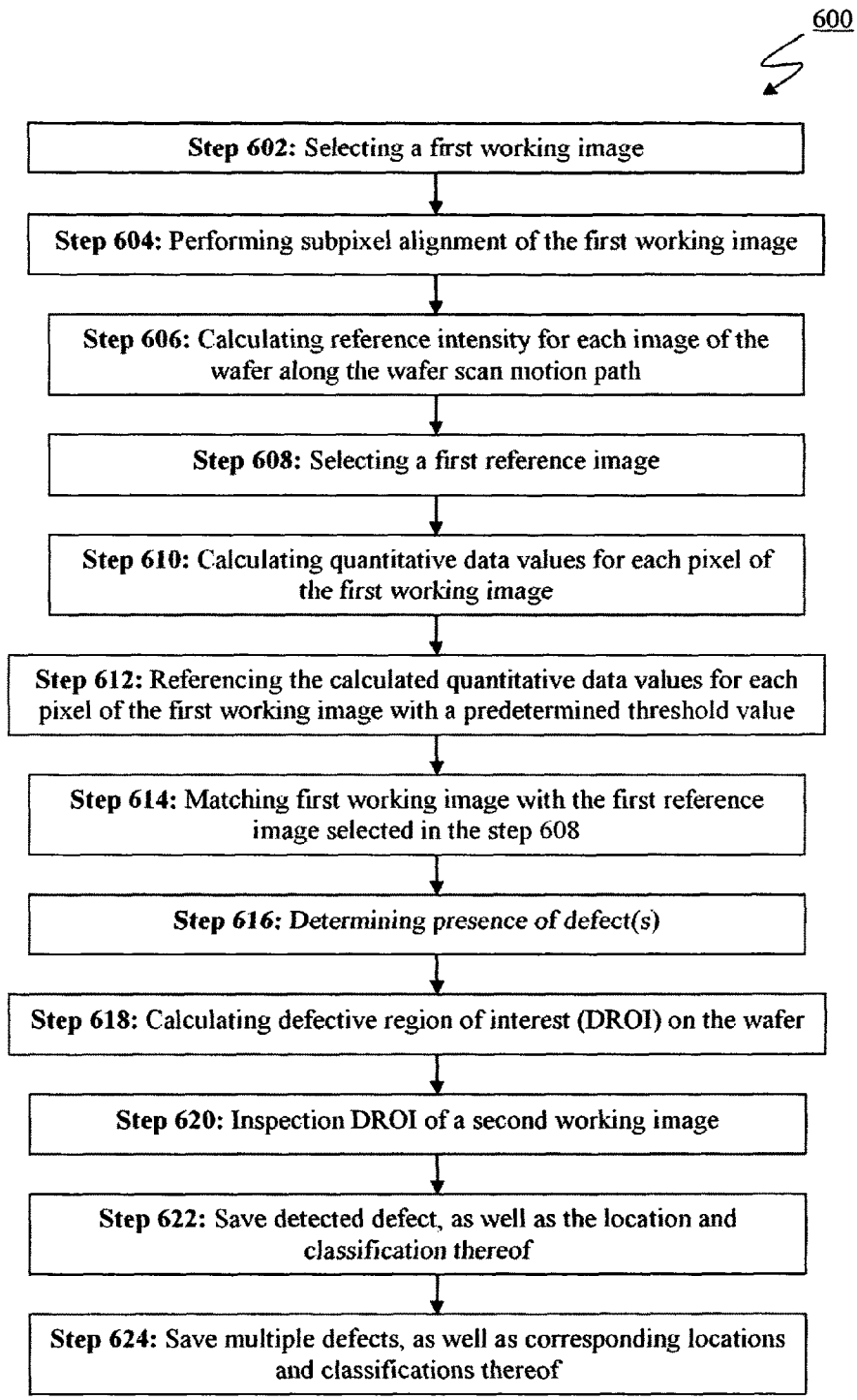
FIG. 23 is a process flow diagram of an exemplary two dimensional image processing process performed in a method step of the method of FIGS. 17A and 17B.

In a step 416 of the method 400, an exemplary two-dimensional (2D) image processing process 600 is performed for at least one of identifying or detecting, classifying, consolidating and storing defects on the semiconductor wafer 12. A process flow diagram of the exemplary 2D image processing process 600 is shown in FIG. 23.

Exemplary 2D Image Processing Process 600

The 2D image processing process 600 facilitates processing of the images captured in the 2D wafer scanning process 500. In addition, the 2D image processing process 600 facilitates at least one of identifying or detecting, classifying, consolidating and storing defects on the semiconductor wafer 12.

In a step 602 of 2D image processing process 600, a first working image is selected and loaded in a memory workspace. The first working image is selected from the number of first images and second images captured and saved during the 2D wafer scanning process. For purposes of the present description, the first working image represents the first image captured by the first image capture device 32 during the 2D wafer scanning process 500.

In a step 604, sub-pixel alignment of the first working image is performed. Sub-pixel alignment is performed using pattern matching techniques using one or more templates. It is performed using one of binary or grey scale or geometrical pattern matching methods. Once aligned, reference intensity for each image is calculated from one or more predefined region of interests in the image as shown in a step 606. The steps 604 and 606 may be collectively referred to as a preprocessing of the first working image. It can be readily appreciated that the preprocessing is not limited to above steps. Additional steps can be incorporated for the preprocessing if necessary.

In a subsequent step 608, a first golden reference or reference image is selected. The first reference image selected in the step 608 corresponds or matches with the first working image. Preferably, the first reference image is selected from a database or collection of golden references or reference images created by the exemplary reference creation process 900 in the step 412 of the method 400. The exemplary reference creation process 900 is described in detail above, and shown in FIGS. 18A and 18B.

In a step 610, quantitative data values for each pixel of the first working image are calculated. In a step 612, the calculated quantitative data values for each pixel of the first working image are referenced with a predetermined threshold value together with multiplicative or additive factors.

In a step 614, the first working image is then matched or evaluated against the first reference image selected in the 608. The matching or evaluation of the first working image with the first reference image facilitates detection or identification of defects on the semiconductor wafer 12. Preferably, the CPU is programmed for effecting automated matching between the first working image and the first reference image. The programmable controller preferably carries out a series of computing instructions or algorithms for matching the first working image with the first reference image to thereby enable the detection or identification of defects on the semiconductor wafer 12.

Determination of presence of one or more defects occurs in a step 616 of the 2D image processing process 600. If more than one defects are detected or identified in the step 616, the algorithm would sort the defects from the largest to the shortest based on either one or all of area, length, width, contrast, compactness, fill factor, edge strength among others. Further the algorithm selects only those defects which meets user defined criteria to calculate defective region of interest (DROI). If a defect (or more than one defects) is detected or identified in the step 616, DROI on the semiconductor wafer 12 is then calculated in a step 618. Preferably, the DROI is calculated dynamically by the CPU in the step 618. The CPU is preferably programmed (i.e. comprises or embodies a series of computing instructions or software) for enabling the calculation of the DROI.

In a step 620, a corresponding DROI of a second working image is inspected. More specifically, the second working image is the second image captured by the second image capture device 34 during the 2D wafer scanning process 400. This is to say, the DROI of the second image (which is a corresponding image of the first image), is inspected in the step 620 after performing sub-pixel alignment of second working image. The inspection of the DROI of the second working image preferably facilitates confirmation of defect detected in the step 616. Further preferably, the step 620 facilitates classification of defect detected in the step 606.

The system 10 processes the DROIs of the second working image instead of the entire image. In addition, in the step 616, if there is no defect found, the method would skip the steps 618 onwards. This will further reduce the amount resources or processing band width needed for processing the second working image. It can be readily appreciated that such intelligent processing sequence dynamically decides based on the results of preceding steps. This will facilitate improved system 10 throughput or wafers per hour.

In a step 622, the detected defect, more specifically the location or position of defect as well as the classification thereof, is saved. Preferably, the detected defect, and the location and classification thereof, is saved in the database of the CPU. Alternatively, the detected defect, and the location and classification thereof, is saved in an alternative database or memory space.

The steps 602 to 622 can be repeated or looped any number of times for processing the images captured during the 2D wafer scanning process 500. Each of the images captured during the 2D wafer scanning process 500 is sequentially loaded in the memory workspace and processed for facilitating the detection of defects, which may be present on the semiconductor wafer 12. The steps 602 to 622, and the repetition thereof, facilitates at least one of detection, confirmation, and classification of defects, which may be present on the semiconductor wafer 12 at any of the multiple image capture positions along the wafer scan motion path.

In a step 624, each of multiple defects, and the locations and classifications thereof, detected by the 2D image processing process 600 are consolidated and saved, preferably in the database of the CPU. Alternatively the defects, and the locations and classifications thereof, are consolidated and saved in an alternative database or memory space.

The 2D image processing process is preferably an automated process. Preferably, the CPU is programmed for, or comprises a series of computing instructions or software program, for automatically performing the 2D image processing process. Alternatively, the 2D image processing process may be facilitated by an at least one manual input as required.

Completion of the 2D image processing process 600 of the step 416 of the method 400 results in consolidation and storage of defects, and the locations and classifications thereof, detected using the brightfield illumination, the DHA illumination and DLA illumination.

Figure 24:
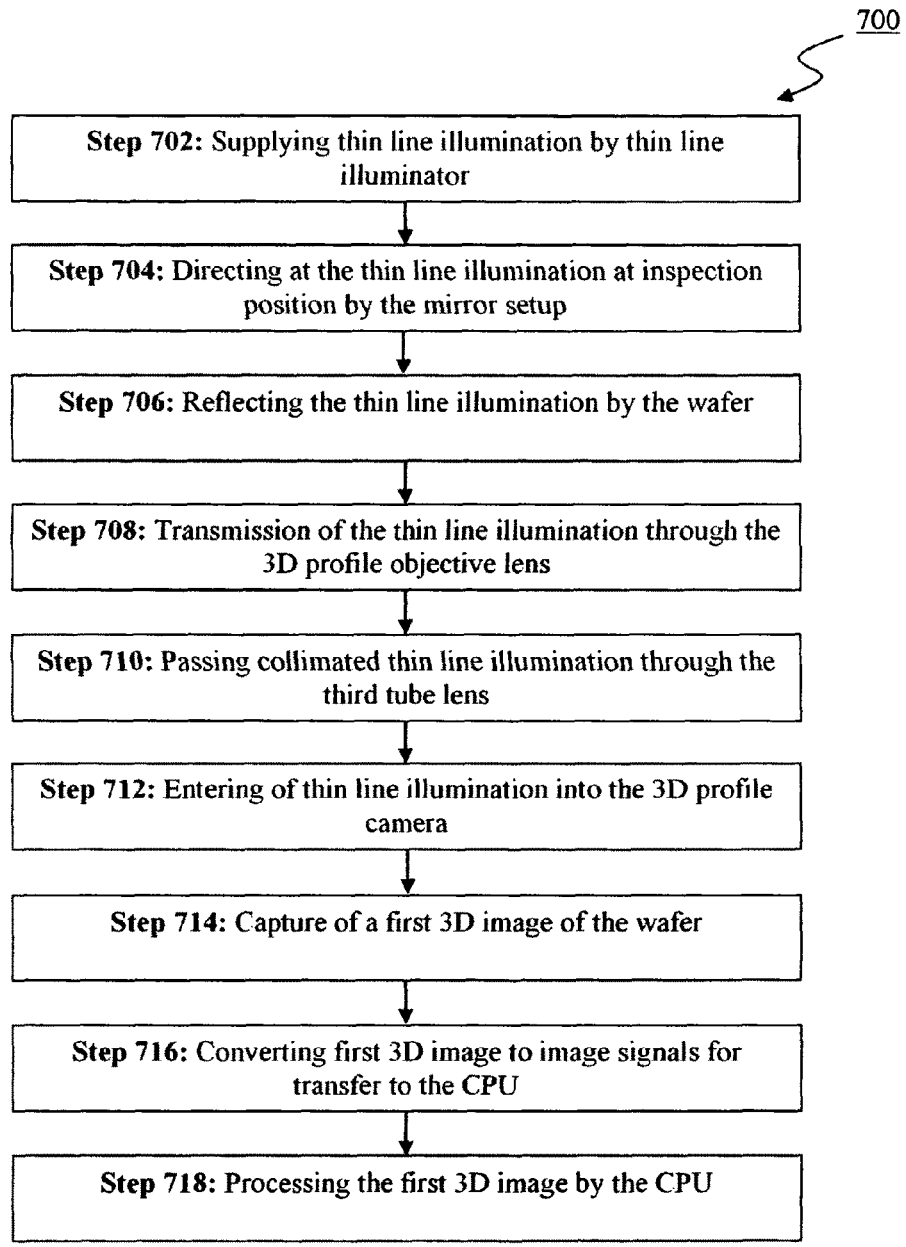
FIG. 24 is a process flow diagram of a first exemplary three dimensional wafer scanning process performed in a method step of the method of FIGS. 17A and 17B.

In a subsequent step 418 of the method 400, a first exemplary three-dimensional (3D) wafer scanning process 700 is performed. Preferably, the first 3D wafer scanning process 700 enables capture of 3D profile images of the semiconductor wafer 12, for facilitating consequent formation of a 3D profile of the semiconductor wafer 12. The semiconductor wafer 12 is displaced along the calculated wafer scan motion path for capturing 3D images of the semiconductor wafer 12 at any one or more of the multiple images capture positions along the wafer scan motion path as calculated in the step 408. A process flow diagram of the first exemplary 3D wafer scanning process 700 is shown in FIG. 24.

Exemplary 3D Wafer Scanning Process 700

In a step 702 of the 3D wafer scanning process, thin line illumination is supplied by or emitted from the thin line illuminator 52. In a step 704, the thin line illumination is directed at the inspection position by the mirror setup 54.

In a subsequent step 706, the thin line illumination is reflected by the semiconductor wafer 12, or portion thereof, positioned at the inspection position. Reflected thin line illumination from the semiconductor wafer 12 is transmitted through the 3D profile objective lens 58 which has aberration corrected in infinity, in a step 708. Transmission of the thin line illumination through the 3D profile objective lens 58 in the step 708 collimates the thin line illumination.

In a step 710, the collimated thin line illumination then passes through the tube lens 60 before entering the 3D profile camera 56 in a step 712. The tube lens 60 preferably focuses the collimated thin line illumination onto the image capture plane of the 3D profile camera 56. Thin line illumination focused on the 3D image capture plane enables capture of a first 3D profile image of the semiconductor wafer 12 in a step 714. Collimation of the thin line illumination between the 3D profile objective lens 58 and the tube lens 60 facilitates ease of introduction of optical components or accessories therebetween, and enable flexible positioning and reconfiguration of the 3D profile camera 56.

As previously mentioned, the thin line illumination is supplied by a laser or broadband fiber optic illumination source. In addition, the thin line illumination is preferably directed at the inspection position at a specified angle with reference to a horizontal plane of the semiconductor wafer 12 positioned thereat. The angle at which the thin line illumination is directed at the inspection position is preferably variable as required using techniques known to a person skilled in the art. It will also be appreciated by a person skilled in the art that the wavelength of the thin line illumination may be selected, and varied, as required. Preferably, the broadband wavelength of the thin line illumination is selected for enhancing accuracy of at least one of defect detection, verification, and classification.

The first 3D image is converted to image signals and transmitted to the CPU in a step 716. In a step 718, the first 3D image is processed by the CPU for at least one of 3D height measuring, Coplanarity measuring, detecting and classifying a defect.

Preferably the steps 702 to 718 can be repeated any number of times for capturing a corresponding number of 3D images, and for transmitting the captured 3D images to the CPU. The steps 702 to 718 can be performed either at selected image capture positions along the wafer scan motion path or the whole wafer.

Preferably, the first 3D wafer scanning process 700 enhances accuracy with which the exemplary method 300 inspects a semiconductor wafer. More specifically, the first 3D wafer scanning process 700 enhances accuracy of defect detection by the method 300. Such inspection provides details 3D metrological details such coplanarity, height of three dimensional structures such as solder balls, gold bumps, warpage of individual die as well as whole wafer.

Preferably, results of the step 718, and repetitions thereof, of processing of 3D images are saved in the database of the CPU. Alternatively, results of the step 718, and repetitions thereof, of processing of 3D images are saved in an alternative database or memory space as required.

Figure 25:
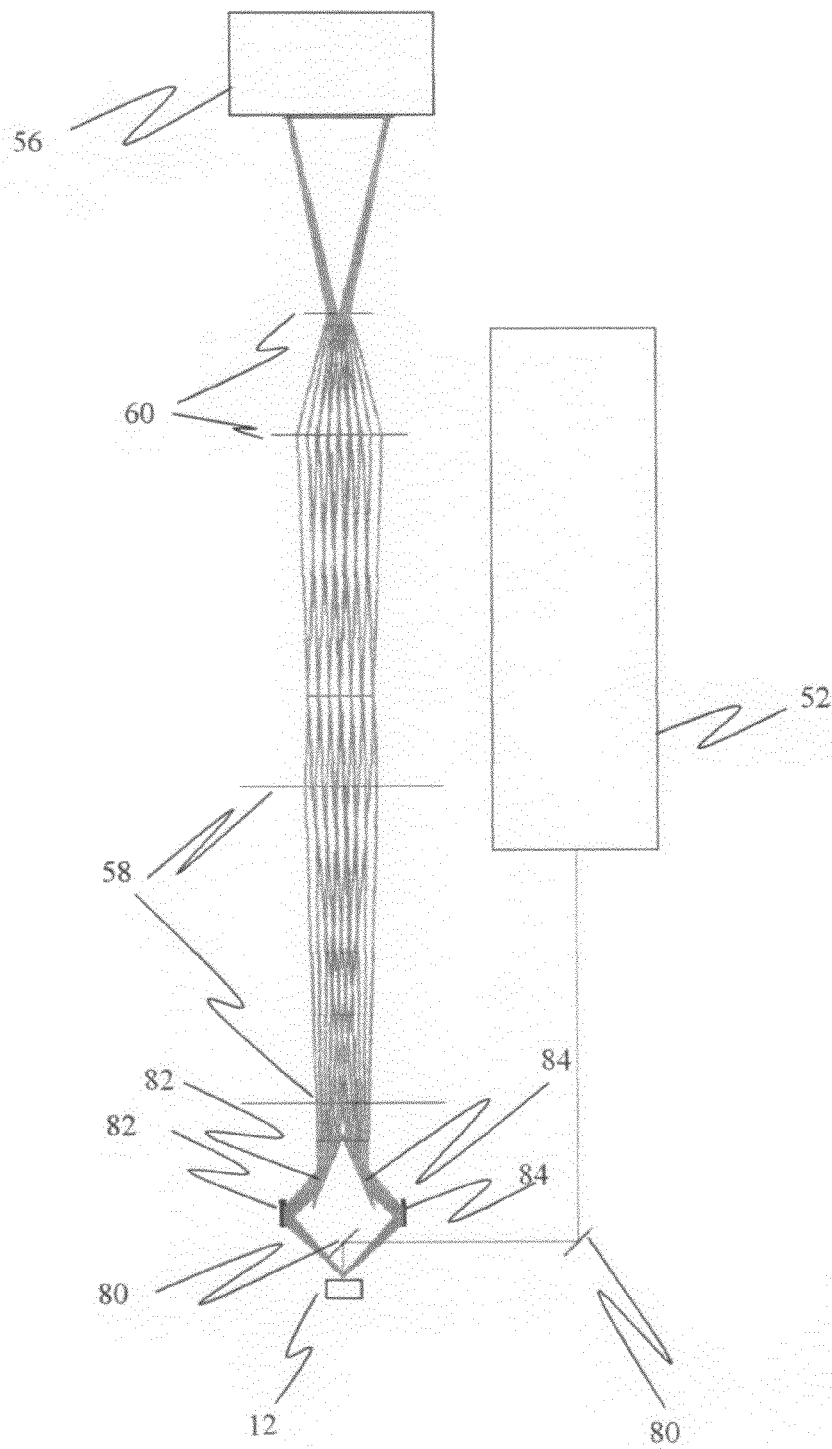
FIG. 25 shows an exemplary optical ray path of illumination between a thin line illuminator a 3D image capture device or camera of the system of FIG. 1.
Figure 26:
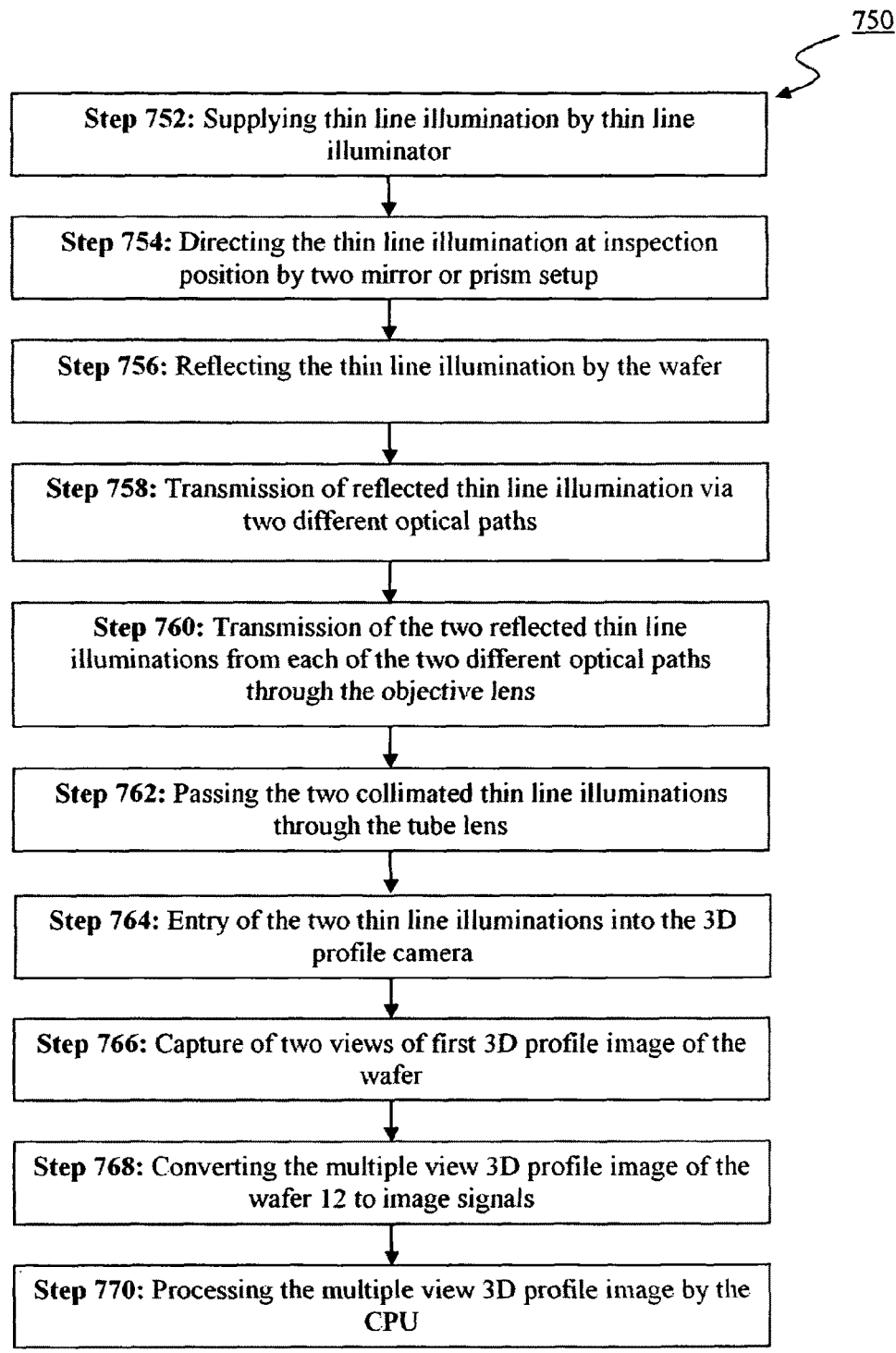
FIG. 26 is a process flow diagram of a second exemplary three dimensional wafer scanning process performed in a method step of the method of FIGS. 17A and 17B.

An exemplary second three-dimensional (3D) wafer scanning process 750 can also be used instead of the first exemplary 3D wafer scanning process 700. The optical ray path of the exemplary second 3D wafer scanning process 750 is shown in FIG. 25 and a corresponding process flow diagram of the exemplary second 3D wafer scanning process 750 is as shown in FIG. 26.

In a step 752 of the second 3D wafer scanning process 750, the thin line illuminator 52 supplies thin line illumination. In a step 754, the thin line illumination is directed at the inspection position by a reflector assembly 80. The reflector assembly 80 is alternatively known as a prism assembly or a two mirror or prism setup.

In a step 756, the thin line illumination is reflected by the semiconductor wafer 12. Thin line illumination reflected by the semiconductor wafer 12 can be reflected in different directions depending on the surface profile of the semiconductor wafer 12. For example, structural and geometrical variations on the semiconductor wafer 12 can cause the thin line illumination to be reflected by the semiconductor wafer 12 in different directions (otherwise known as dispersion of illumination).

Depending upon the surface profile of the semiconductor wafer 12, the reflected thin line illumination from the semiconductor wafer 12 can disperse in different directions. Dispersion of the thin line illumination reflected from the semiconductor wafer 12 in multiple directions can make it difficult to obtain an accurate measurement of the surface profile of the semiconductor wafer 12. In other words, the dispersion of thin line illumination reflected from the semiconductor wafer 12 in multiple directions can make it difficult to capture accurate 3D images of the semiconductor wafer 12. This is because the dispersion of the thin line illumination reflected from the semiconductor wafer 12 in multiple directions can result in inappropriately reduced or increased amount of thin line illumination entering the 3D profile camera 56, and thereby in the capture of dimmer or brighter images respectively. It is difficult to derive accurate measurements from images that are too dim or too bright. Accordingly, it is difficult to obtain an accurate surface profile of the semiconductor wafer 12 using images that are too dim or too bright.

Thin line illumination reflected by the semiconductor wafer 12 is received by the reflector assembly 80. More specifically, the reflector assembly 80 is configured for capturing thin line illumination reflected in multiple directions. Preferably, the reflector assembly 80 comprises a first pair of mirrors or prisms 82 and a second pair of mirrors or prisms 84. In a step 758, reflected thin line illumination travels along two optical paths, namely a first optical path via, or as directed by, the first pair of mirrors or prisms 82 and a second optical path via, or as directed by, the second pair of mirrors or prisms 84. It will be understood by a person skilled in the art that the reflector assembly can be configured for directing captured reflected thin line illumination along a different number optical paths as required.

The thin line illumination traveling along each of the first optical path and the second optical path passes through the objective lens 58 in a step 760. The two thin line illuminations passing through the 3D profile objective lens 58 are collimated. The first pair of mirrors or prisms 82 and the second pair of mirrors or prisms 84 are preferably symmetrically positioned.

In a step 762, the two collimated thin line illuminations passes through the tube lens 60. The two thin line illuminations then enters the 3D profile camera 56 in a step 764. The tube lens 60 facilitates focusing of the two thin line illuminations onto the image capture plane of the 3D profile camera 56. Focusing of the two thin line illuminations onto the image capture plane of the 3D profile camera 56 enables capture of two views of a 3D profile image of the semiconductor wafer 12 in a step 766.

Without the use of the reflector assembly 80, the dispersion of the thin line illumination reflected from the semiconductor wafer 12 in multiple directions can result in inappropriately reduced or increased amount of thin line illumination entering the 3D profile camera 56, and thereby in capture of images that are too dim or too bright respectively. Such images are typically discarded. The use of images that are too dim or too bright can result in an inaccurate 3D profiling, or measurement of the surface profile, of the semiconductor wafer 12.

The ability of the system 10 to perform the second 3D wafer scanning process 750 enables capture of two views of the 3D profile of the semiconductor wafer 12 using a single 3D image capture device 56. The two views improve accuracy of the 3D profiling or inspection of the wafer. In addition, the use of the two symmetrically positioned mirrors or prisms 82, 84 enables illumination reflected from the semiconductor wafer 12 in different directions to be re-directed for capture by the 3D image capture device 56. It will be understood by a person skilled in the art that the reflector assembly 80 can be configured for directing illumination reflected from the semiconductor wafer 12 in multiple directions (for example, two, three, four and five directions) to be captured by a single exposure of the 3D image capture device 56.

To receive two views of the same profile of wafers, existing equipments use expensive, bulky and complicated setup by using multiple image capture devices. Due to the inconsistent profile of wafers, reflected rays do not consistently return in a predetermined ray path to the multiple image capture devices. This is to say, the dispersion of illumination due to structural and geometrical variations on the surface of the semiconductor wafer 12 typically results in inaccuracies in single view images captured of the semiconductor wafer 12.

To overcome the variation of the strength and weakness (i.e. the dispersion) of the reflected rays from the semiconductor wafers 12, the present system 10 enables illumination reflected from the semiconductor wafer 12 in different directions to be captured by the 3D image capture device 56. This helps to improve accuracy of 3D profiling and inspection of the semiconductor wafer 12. The use of a single camera, more specifically the 3D image capture device 56, also enhances cost and space efficiency of the system 10. Furthermore, the ability to use a single objective lens and a single tube lens (in this case, the objective lens 58 and tube lens 60) for capturing multiple views of the semiconductor wafer 12 enhances ease and accuracy of calibration.

After completion of the first exemplary 3D wafer scanning process 700 or the second exemplary 3D wafer scanning process 750, all the detected defects, and the locations and classifications thereof, on the semiconductor wafer 12 obtained by performing the steps 416 and 418 are preferably consolidated. The consolidation of the defects, and the locations and classifications thereof, facilitates calculation of a review scan motion path in a step 420. Preferably, the review scan motion path is calculated based on the locations of defects detected on the semiconductor wafer 12 along the wafer scan motion path. In addition, defect image capture positions along the review scan motion path is calculated or determined in the step 420. The defect image capture positions preferably correspond with the locations on the semiconductor wafer 12 at which defects were detected (i.e. the DROI of the semiconductor wafer 12) during the steps 416 and 418.

Figure 27:
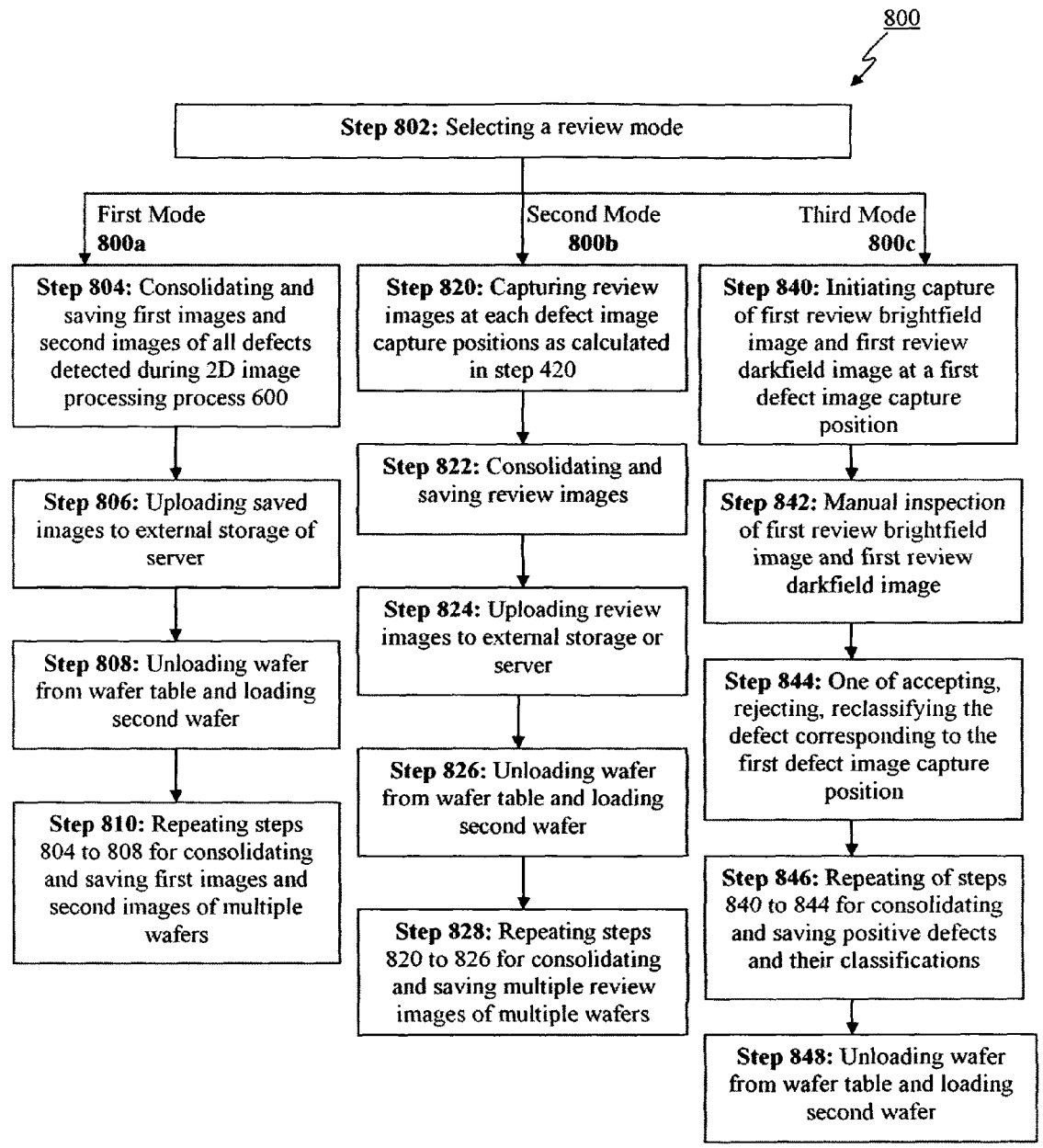
FIG. 27 is a process flow diagram of an exemplary review process performed in a method step of the method of FIGS. 17A and 17B.

In a step 422 of the exemplary method 400, an exemplary review process 800 is performed. The review process 800 enables review of defects detected in the steps 416 and 418. Preferably, the review process 800 occurs via at least one of a first mode 800a, a second mode 800b and a third mode 800c. A process flow chart of the exemplary review process 800 is shown in FIG. 27.

Exemplary Review Process 800

As previously mentioned, the review process 800 preferably comprises three review modes, namely the first mode 800a, the second mode 800b and the third mode 800c. In a step 802, a review mode (i.e. one the first mode 800a, the second mode 800b and the third mode 800c) is selected.

First Mode 800a of the Review Process 800

In a step 804 of the first mode 800a of the review process 800, the first images and the second images of all the defects detected during the 2D image processing process 600 performed in the step 416 of the method 400 are consolidated and saved.

In a step 806, the consolidated and saved first images and second images of the defects detected on the semiconductor wafer 12 are uploaded or transferred to an external storage or server for an offline review.

In a step 808, the semiconductor wafer 12 (i.e. the current semiconductor wafer 12 on the wafer table 16) is unloaded and a second wafer is loaded from the wafer stack 20 onto the wafer table 16 by the robotic arm. In a step 810, each of the steps 804 to 808 is repeated for the second wafer.

The steps 804 to 810 are sequentially repeated any number of times, depending on the number of wafers of the wafer stack 20. Repetition of the step 804 to 810 results in consolidation and saving of the first images and second images obtained for each wafer of the wafer stack 20, and the uploading of the first images and the second images, to the external storage or server for an offline review. It will be appreciated by a person skilled in the art that the first mode 800*a* enables automated performance of the steps 804 to 810 without need for user intervention and without affecting production. This method allows continuing production while user can perform offline review of saved images. This method increases system 10 utilization as well as productivity.

Second Mode 800*b* of the Review Process 800

In a step 820 the second mode 800*b* of the review process 800, a number of review images is captured at each of the defect image capture positions as calculated in the step 420. More specifically, a review brightfield image and a review darkfield image are captured at each of the defect image capture positions as calculated in the step 420 using review image capture device 60 shown in FIG. 14. This is to say s review brightfield image using brightfield illuminator 62 and a review darkfield image using darkfield illuminator 64 are captured of each defect detected by the 2D image processing process 600 of the step 416. Each of the number of review images is captured by the review image capture device 60. Preferably, each of the number of review images is a colored image.

It will be understood by a person skilled in the art, provided with the disclosure of the present description that intensities of the brightfield illumination and darkfield illumination used for capturing the brightfield review images and darkfield review images respectively may be determined and varied as required. For example, the intensities of illumination used for capturing the number of review images may be selected based on type of wafer defect the user of the system 10 wishes to review or based on the material of semiconductor wafer 12. It is also possible to capture multiple review images using various combinations and various intensity levels of brightfield and darkfield illumination set by the user.

In a step 822, the number of review images captured at each of the defect image capture positions as calculated in the step 420 are consolidated and saved. The consolidated and saved review images captured at each of the defect image capture positions are then uploaded to the external storage or server for offline review in a step 824.

In a step 826, the semiconductor wafer 12 (i.e. the current semiconductor wafer 12 on the wafer table 16) is unloaded and a second semiconductor wafer 12 is loaded from the wafer stack 20 onto the wafer table 16 by the robotic wafer handler 18. In a step 828, each of the steps 402 to 422 is repeated for the second semiconductor wafer 12. Consolidated and saved first images and second images of defects detected on the second semiconductor wafer 12 are uploaded to the external storage or server.

In the second mode 800*b* of the review process 800, the steps 820 to 828 can be repeated any number of times, depending on the number of semiconductor wafer 12 of the wafer stack 20. Repetition of the steps 820 to 828 results in consolidation and saving of the captured brightfield review images and darkfield review images obtained for each wafer of the wafer stack 20, and the uploading of the first images and the second images, to the external storage or server for an offline review.

This method allows continuing production while user can perform offline review of saved images. This method allows capturing multiple images of each defect at various combinations illuminations for offline review without affecting machine utilization and improves productivity.

Third Mode 800*c* of the Review Process 800

The third mode 800*c* of the review process 800 is preferably initialized by a manual input, more specifically an input or command by the user. In a step 840, the user captures a first review brightfield image and a first review darkfield image at a first defect image capture position. In a step 842, the user manually inspects or reviews the first review brightfield image and the first review darkfield image captured. Preferably, the first review brightfield image and the first review darkfield image are displayed on a screen or monitor for facilitating visual inspection thereof by the user. The user is able to view the defect at different illumination combination using the brightfield and the darkfield illuminator.

In a step 844, the user either accepts or rejects or reclassifies the defect corresponding to the first defect image capture position. The steps 840 to 844 are then sequentially repeated for each and every defect image capture positions as calculated in the step 420.

After the steps 840 to 844 are sequentially repeated for each and every defect image capture positions, positive defects and their classifications are then consolidated and saved in a step 846. The consolidated and saved positive defects and their classifications are then uploaded or transferred to the external storage or server in a step 848. In the third mode 800*c* of the review process 800, the semiconductor wafer 12 (i.e. the current semiconductor wafer 12 on the wafer table 16) is only unloaded after the completion of the step 846. Accordingly, it will be appreciated by a person skilled in the art that the third mode 800*c* of the review process requires continuous user presence for effecting the visual inspection or review of each wafer.

In a step 848 of the review process 800, the semiconductor wafer 12 (i.e. the current semiconductor wafer 12 on the wafer table 16) is unloaded and the robotic wafer handler 18 then loads a second semiconductor wafer 12 onto the wafer table 16 from the wafer stack 20. The steps 840 to 848 are repeated any number of times depending on the number of semiconductor wafers 12 to be inspected (or number of semiconductor wafers 12 in the wafer stack 20).

It will be understood by a person skilled in the art with the disclosure provided by the description above that the first mode 800*a* and the second mode 800*b* of the review process effects a relatively indiscriminate consolidation, storage and uploading of captured images to the external storage or server. The first mode 800*a* and the second mode 800*b* represent automated review processes. The user is able to access the external storage or server for offline review of the captured images as and when required. The first mode 800*a* and the second mode 800*b* enable continuous review of each of the wafers of the wafer stack 20, or the continuous image capture, consolidation, upload and storage.

It will be appreciated by a person skilled in the art that while only three review modes, namely the first mode 800*a*, the second mode 800*b* and the third mode 800*c* are described in the present description, a person skilled in the art may employ alternative review processes or different permutations or combinations of the steps of each of the three review modes 800*a*, 800*b* and 800*c*. In addition, it will be appreciated by a person skilled in the art that each of the three review modes 8000*a*, 800*b* and 800*c* may be modified or altered as required using methods known in the art without departing from the scope of the present invention.

After the performance of the review process 800, verified defects, and the locations and classifications thereof, are consolidated and saved in a step 426. The verified defects, and the locations and classifications thereof, are consolidated and saved either in the database or in an external database or memory space. The wafer map is also updated in the step 426.

As previously described, each of the captured brightfield images, DHA images and DLA images is compared with a corresponding golden reference or reference image for identifying or detecting defects on the semiconductor wafer 12. The exemplary reference image creation process 900 provided by the present invention (as shown in FIGS. 18A and 18B) facilitates creation or derivation of such reference images. It will be understood by a person skilled in the art that the reference image creation process 900 can also be referred to as a training process.

As previously described, each of the 2D brightfield images, 2D DHA images, 2D DLA images captured during the 2D wafer scanning process 500 are preferably matched with their corresponding reference images created by the reference image creation process 900.

An exemplary comparison process is already described with the 2D image processing process 600. However, for increased clarity, a summary of matching between working images and reference images is provided below. Firstly, sub-pixel alignment of the selected working image is performed using known references including, but not limited to, templates, trace, bumps, pads and other unique patterns. Secondly, the reference intensity of the semiconductor wafer 12 at the image capture position at which the working image was captured is calculated. An appropriate reference image for matching with the working image is then selected. The appropriate reference image is preferably selected from the multiple reference images created by the reference image creation process 900.

The CPU is preferably programmed for enabling selection and extraction of the appropriate reference image to which the working image will be matched. Preferably, the calculation, and storage, of the normalized average or geometric mean, standard deviation, maximum and minimum intensity of each pixel of the reference images by the reference image creation process 900 enhances speed and accuracy of extracting the appropriate reference image to which the working image will be compared.

Corresponding quantitative data for each pixel of the working image is then calculated. The quantitative data is for example normalized average or geometric mean, standard deviation, maximum and minimum intensities of each pixel of the working image. The quantitative data values for each pixel of the working image is then referenced or checked against corresponding data values of each pixel of the selected reference image.

Comparison of quantitative data values between pixels of the working image and pixels of the reference image enables identification or detection of defects. Preferably, predetermined threshold values are set by the user. Difference between the quantitative data values of pixels of the working image and pixels of the reference image is matched against the predetermined threshold values with one of multiplicative, additive and a constant value. If the difference between the quantitative data values of pixels of the working image and pixels of the reference image is greater than the predetermined threshold values, a defect (or defects) is flagged.

The predetermined threshold value can be varied as required. Preferably, the predetermined threshold value is varied for adjusting stringency of the method 400. In addition, the predetermined threshold value is preferably varied as required depending on type of defect to be detected, material of semiconductor wafer 12 presented for inspection, or illumination conditions. Furthermore, the predetermined threshold value may be altered depending on a customer's or more generally the semiconductor industry's, requirements.

An exemplary system 10 and an exemplary method 400 for inspecting semiconductor wafers are described above. A person skilled in the art provided with the description above will understand that the modifications to the system 10 and the method 400 may be done without departing from the scope of the present invention. For example, sequence of steps of the method 400, and the sequence of steps of processes 500, 600, 700, 750, 800 and 900, may be modified without departing from the scope of the present invention.

It is an objective of the system 10 and method 400 of the present invention to enable accurate and cost-effective inspection of semiconductor wafers. The ability for an automated inspection of semiconductor wafers by the system 10 and the method 400 while the semiconductor wafer is in motion enhances efficiency of the inspection of semiconductor wafers. This is because time is not wasted for decelerating and stopping of individual semiconductor wafers at an inspection position for image capture thereof, and for subsequent acceleration and transport of the semiconductor wafer from the inspection position after the images have been captured, as with several existing semiconductor wafer inspection systems. Known image offsets between multiple image captures facilitate processing of the captured images to thereby detect defects that may be present therein. The offset relative to the particular set of images for the same semiconductor wafer enables the software to accurately determine the co-ordinates of the defect in the semiconductor wafer and, subsequently, the position of the semiconductor wafer in the entire frame. The offset is preferably determined by reading the encoder values in both the X- and Y-displacement motors and is used to calculate the co-ordinates of a defect or defects. In addition, the use of two images at every inspect locations combines advantages of two different imaging techniques for facilitating more accurate semiconductor wafer inspection.

It will also be understood by a person skilled in the art that the time-synchronization of image captures can be altered as required. More specifically, the time-synchronization may be adjusted for enhancing the ability of the programmable controller to compensate for image offset between the captured images. The system 10 and method 400 of the present invention facilitates accurate synchronization between supply of illumination and exposure of corresponding image capture devices for capturing of images to minimize degradation of inspection quality.

Illuminations used with the system 10 can be in the full visible spectrum of light for capture of enhanced quality images. Intensities of illumination and their combinations supplied for capture of images by the system 10 can be easily selected and varied as required depending on factors including, but not limited to, type of defects to be detected, material of the semiconductor wafer and stringency of semiconductor wafer inspection. The system 10 and method 400 provided by the present invention also enables measurement of height of 3D elements on the semiconductor wafer, and analysis of 3D profile images while the semiconductor wafer is moving.

The system 10 of the present invention has an optical setup (i.e. optical inspection head 14), which does not require frequent spatial reconfigurations to cater to changes in semiconductor wafer structure or characteristics. In addition, the use of tube lenses with the system 10 enables ease of reconfiguration and design of the system 10, more specifically of the optical inspection head 14. The use of tube lenses enhances ease of introduction of optical components and accessories into the system, more specifically between objective lenses and the tube lenses.

The system 10 of the present invention comprises vibration isolators 24 (collectively known as a stabilizer mechanism) for buffering unwanted vibrations to the system 10. The vibration isolators 24 helps to enhance quality of images captured by the first image capture device 32, the second image capture device 34, the 3D profile camera and the review image capture device 62, and thus the accuracy of defect detection. In addition, the XY-displacement table 22 of the system 10 enables accurate displacement and alignment of the semiconductor wafer relative the inspection position.

As described in the background, existing reference image derivation or creation processes requires manual selection of "good" semiconductor wafers, resulting in relative inaccuracies and inconsistencies of derived reference images. Accordingly, quality of semiconductor wafer inspection is adversely affected. The system 10 and method 400 of the present invention achieves enhanced quality of inspection by creating reference images without manual selection (i.e. subjective selection) of "good" semiconductor wafers. The reference image creation process 900 allows for application of different thresholds of intensities across different locations of the semiconductor wafer, thus accommodating non-linear illumination variations across the semiconductor wafer. The method 400 therefore facilitates reduction in false or unwanted detection of defects and ultimately an enhanced quality of semiconductor wafer inspection.

The present invention enables automated defect detection using an analytical model that compares reference images with captured images of unknown quality semiconductor wafers. The present invention also enables automated defect detection, preferably by performing digital analysis on digitalized images (i.e. working images and reference images).

The present invention enables automated review mode (or on offline review) without affecting production and improves machine utilization, whereas the existing equipment offers only manual review mode, which require the operator to decide every defect by using and looking at multiple different illumination intensities.

In the foregoing manner, an exemplary system and an exemplary method for inspecting semiconductor wafers and components provided by embodiments of the present invention are described. The exemplary system and method addresses at least one of the issues or problems faced by existing semiconductor inspection systems and methods as mentioned in the background. It will however be understood by a person skilled in the art that the present invention is not limited to specific forms, arrangements or structures of the embodiments described above. It will be apparent to a person skilled in the art in view of this disclosure that numerous changes and/or modifications can be made without departing from the scope and spirit of the invention.

The invention claimed is:

1. A method for inspecting a wafer comprising:
    capturing a plurality of images of at least one region of at least a first wafer, each wafer being of an unknown quality, each of the plurality of captured images being captured using a predetermined contrast illumination, each of the plurality of captured images comprising a plurality of pixels;
    determining a plurality of reference intensities for each of the plurality of pixels of each of the plurality of captured images based on a plurality of statistical parameters;
    deriving at least one golden reference image from the plurality of captured images;
    capturing an image of a region of a second wafer, the second wafer being of an unknown quality;
    selecting a first golden reference image from the at least one golden reference image; and
    comparing the captured image of the region of the second wafer with the first golden reference image to thereby determine at least one of presence and type of defect on the second wafer.

2. The method as in claim 1, further comprising:
    calculating a plurality of weighted indices associated with the plurality of reference intensities for each of the plurality of pixels of each of the plurality of captured images,
        wherein the plurality of weighted indices comprises at least one statistical parameter including a geometric mean, a range a standard deviation and a maximum and a minimum of the plurality of reference intensities, each weighted index within the plurality of weighted indices being a value determined by (a) applying a weighting to any of the at least one statistical parameter, or (b) a combination of any number of the weighted indices.

3. A system for inspecting a wafer, the system comprising:
    means for performing a training process for obtaining at least one golden a reference image, the training process comprising:
    capturing a plurality of images of at least one region of at least a first wafer, each wafer being of an unknown quality, each of the plurality of captured images being captured at one of a plurality of predetermined contrast illuminations, each of the plurality of captured images comprising a plurality of pixels,
    determining a plurality of reference intensities of each of the plurality of pixels of each of the plurality of captured images based on a plurality of statistical parameters;
    deriving at least one golden reference image from the plurality of captured images;
    means for capturing an image of a region of a second wafer, the second wafer being of an unknown quality;
    means for selecting a first golden reference image from the at least one golden reference image;
    means for comparing the captured image of the region of the second wafer with the first golden reference image to thereby determine at least one of presence and type of defect on the second wafer, and
    means for calculating a plurality of weighted indices for the plurality of reference intensities of each of the plurality of pixels of each of the plurality of captured images,
    wherein the plurality of weighted indices comprises at least one statistical parameter including a geometric mean, a range, a standard deviation, and a maximum and a minimum of the plurality of reference intensities, each weighted index within the plurality of weighted indices being a value determined by (a) applying a weighting to any of the at least one statistical parameter, or (b) a combination of any number of the weighted indices.

4. A non-transitory machine readable medium, tangibly embodying a program of instructions stored on the non-transitory machine readable medium, the program of instructions executable by a machine to perform method steps for inspecting a wafer, the method steps comprising the steps of:
    performing a training process for creating at least one golden reference image, the training process comprising:
        capturing a plurality of images of at least one region of at least a first wafer, each wafer being of an unknown quality, each of the plurality of captured images being captured at one of a plurality of predetermined contrast illuminations, each of the plurality of captured images comprising a plurality of pixels;

determining a plurality of reference intensities of each of the plurality of pixels of each of the plurality of captured images based on a plurality of statistical parameters;

deriving at least one golden reference image from the plurality of captured images;

capturing an image of a region of a second wafer, the second wafer being of an unknown quality;

selecting a first golden reference image from the at least one golden reference image;

comparing the captured image of the region of the second wafer with the first golden reference image to thereby determine at least one of presence and type of defect on the second wafer; and calculating a plurality of weighted indices for the plurality of reference intensities of each of the plurality of pixels of each of the plurality of captured images, wherein the plurality of weighted indices comprises at least one statistical parameter including a geometric mean, a range, a standard deviation, and a maximum and a minimum of the plurality of reference intensities, each weighted index within the plurality of weighted indices being a value determined by (a) applying a weighting to any of the at least one statistical parameter, or (b) a combination of any number of the weighted indices, and wherein the program instructions stored on the non-transitory machine readable medium are retrievable from the non-transitory machine readable medium and executable by a processing unit of the machine.

5. The method of claim 1, further comprising performing a training process for creating golden reference images for inspecting a wafer.

6. The method of claim 2, further comprising performing a training process for creating golden reference images for inspecting a wafer.

7. The method of claim 1, wherein the plurality of predetermined contrast illuminations comprises:
at least one of a brightfield broadband illumination and a darkfield broadband illumination.

8. The method of claim 6, wherein the method of performing the training process comprises:
aligning each of the plurality of captured images of the first wafer.

9. The method of claim 8, wherein the method of performing the training process further comprises:
registering sub pixels of each of the plurality of captured images of the first wafer, the registering being performed with reference to at least one predetermined feature on the wafer.

10. The method of claim 6, wherein the method of performing the training process further comprises:
storing each of the plurality of golden reference images and plurality of statistical parameters.

11. The method of claim 1, wherein comparing the captured image of the region of the second wafer with the first golden reference image comprises:
extracting features from the captured image and extracting features from the first golden reference image;
matching features of the captured image and features of the first golden reference image to identify defects on the second wafer; and
comparing features of the captured image and features of the first golden reference image by way of:
computing feature properties of the captured image and computing feature properties of the first golden reference image; and
matching the computed feature properties of the captured image and computed feature properties of the first golden reference image,
wherein the computed feature properties comprises at least one of average intensity, standard deviation of intensity, range of intensity, minimum intensity and maximum intensity.

12. The method of claim 11, further comprising:
aligning the captured image of the region of the second wafer with the first golden reference image prior to matching the computed feature properties of the captured image with the computed feature properties of the first golden reference image.

13. The method of claim 12, wherein the captured image of the region of the second wafer and the first golden reference image are captured using a similar predetermined contrast illumination.

14. A method for inspecting a wafer, comprising:
capturing a plurality of images of at least one region of at least a first wafer, each wafer being of an unknown quality, each of the plurality of captured images being captured using a predetermined contrast illumination, each of the plurality of images comprising a plurality of pixels;
determining a plurality of reference intensities for each of the plurality of pixels of each of the plurality of captured images based on a plurality of statistical parameters;
deriving at least one golden reference image from the plurality of captured images;
capturing an image of a region of a second wafer, the second wafer being of an unknown quality;
selecting a first golden reference image from the at least one golden reference image; and
comparing the captured image of the region of the second wafer with the first golden reference image to thereby determine at least one of presence and type of defect on the second wafer, wherein comparing the captured image of the region of the second wafer with the first golden reference image comprises:
extracting features from the captured image and extracting features from the first golden reference image;
matching features of the captured image and features of the first golden reference image to identify defects on the second wafer, comparing features of the captured image and features of the first golden reference image comprising:
computing feature properties of the captured image and computing feature properties of the first golden reference image; and
matching the computed feature properties of the captured image and computed feature properties of the first golden reference image,
wherein the computed feature properties comprises at least one of average intensity, standard deviation of intensity, range of intensity, minimum intensity and maximum intensity.

15. The method as in claim 1, wherein deriving the at least one golden reference image includes discarding images having pixels with reference intensities outside of a predetermined limit, range, or standard deviation.

16. The method as in claim 1, wherein capturing a plurality of images of at least one region of at least a first wafer comprises capturing a plurality of images of corresponding regions across multiple wafers.

17. The system as in claim 3 wherein deriving the at least one golden reference image includes discarding images having pixels with reference intensities outside of a predetermined limit, range, or standard deviation.

18. The system as in claim 3, wherein capturing a plurality of images of at least one region of at least a first wafer comprises capturing a plurality of images of corresponding regions across multiple wafers.

19. The non-transitory machine readable medium as in claim 4, wherein deriving the at least one golden reference image includes discarding images having pixels with reference intensities outside of a predetermined limit, range, or standard deviation.

20. The non-transitory machine readable medium as in claim 4, wherein capturing a plurality of images of at least one region of at least a first wafer comprises capturing a plurality of images of corresponding regions across multiple wafers.

21. The method as in claim 14, wherein deriving the at least one golden reference image includes discarding images having pixels with reference intensities outside of a predetermined limit, range, or standard deviation.

22. The method as in claim 14, wherein capturing a plurality of images of at least one region of at least a first wafer comprises capturing a plurality of images of corresponding regions across multiple wafers.

* * * * *